US008969585B2

(12) United States Patent
Onomura et al.

(10) Patent No.: US 8,969,585 B2
(45) Date of Patent: Mar. 3, 2015

(54) METHOD FOR PRODUCING OPTICALLY ACTIVE COMPOUND OR SALT THEREOF

(75) Inventors: Osamu Onomura, Nagasaki (JP); Yutaro Tsuda, Nagasaki (JP); Masami Kuriyama, Nagasaki (JP); Toshiharu Yanagi, Hyogo (JP); Kazuya Kodama, Hyogo (JP)

(73) Assignee: Nagasaki University, Nagasaki (JP)

( * ) Notice: Subject to any disclaimer, the term of this patent is extended or adjusted under 35 U.S.C. 154(b) by 70 days.

(21) Appl. No.: 13/982,707

(22) PCT Filed: Jan. 31, 2012

(86) PCT No.: PCT/JP2012/052176
§ 371 (c)(1),
(2), (4) Date: Sep. 18, 2013

(87) PCT Pub. No.: WO2012/105574
PCT Pub. Date: Aug. 9, 2012

(65) Prior Publication Data
US 2014/0012010 A1  Jan. 9, 2014

(30) Foreign Application Priority Data

Jan. 31, 2011  (JP) .................................. 2011-019287
Jul. 11, 2011  (JP) .................................. 2011-153342
Jul. 12, 2011  (JP) .................................. 2011-153692

(51) Int. Cl.
*C07D 263/14* (2006.01)
*C07D 413/04* (2006.01)
*C07B 53/00* (2006.01)
*C07D 417/04* (2006.01)

(52) U.S. Cl.
CPC ............ *C07D 263/14* (2013.01); *C07D 417/04* (2013.01); *C07B 53/00* (2013.01); *C07D 413/04* (2013.01)
USPC .......................................... 548/238; 548/239

(58) Field of Classification Search
CPC ........................... C07D 263/14; C07D 413/04
See application file for complete search history.

(56) References Cited

U.S. PATENT DOCUMENTS 2,556,791 A   6/1951  Billman

FOREIGN PATENT DOCUMENTS

| JP | H04273255 A | 9/1992 |
| JP | 2006219464 A | 8/2006 |
| JP | 2008037865 A | 2/2008 |
| JP | 2008290981 A | 12/2008 |

OTHER PUBLICATIONS

International Preliminary Report on Patentability in corresponding PCT/JP2012/052176 dated Aug. 15, 2013. (English Translation).
Bentama Abdeslem et al., Synthese De Nouveaux Glycosyl α-Aminoesters et Glycosyl β-Aminoalcools Triazoliques Precurseurs de Molecules Tensioactives, J. Mar Chim. Heterocycl., vol. 1, No. 1, pp. 48-54 (2002). (French Language).
Bentama Abdeslem et al., Synthese de Nouveaux Glycosyl ÿ-Aminoesters et Glycosyl ÿ-Aminoalcools Triazoliques Precurseurs de Molecules Tensioactives, J. Mar. Chim. Heterocycl., vol. 1, No. 1, pp. 48-54 (2002). (Partial English Translation).
Billman et al., "Amino Acids. IV. Amino Acids Related to Serine", J. Am. Chem. Soc., vol. 67, pp. 1069-1070, (1945).
International Search Report corresponding in PCT/JP2012/052176 mailed Mar. 27, 2012.
Written Opinion in corresponding PCT/JP2012/052176 mailed Mar. 27, 2012.
Tsuda et al., "Catalytic Asymmetric Desymmetrization for Preparation of Optically Active Oxazoline Derivatives," Graduate School of Biomedical Sciences. (After Jul. 19, 2011).

(Continued)

*Primary Examiner* — Kamal Saeed
(74) *Attorney, Agent, or Firm* — Marshall, Gerstein & Borun LLP

(57) ABSTRACT

Provided is a process for producing an optically active compound represented by Formula (3):

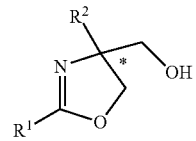

(3)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^2$ is a hydrogen atom or a group which is not reactive in the reaction below; and * represents a chiral center) or a salt thereof by subjecting a compound represented by Formula (1):

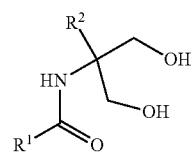

(1)

(wherein $R^1$ and $R^2$ have the same meanings as defined in Formula (3)) to a ring closure reaction in the presence of a chiral ligand having 1 or more coordination sites, a Lewis acid represented by Formula (2):

$$M_mZ_n \qquad (2)$$

(wherein M is a metal ion, Z is a counter anion of M, and m and n are integers of 1 to 4), and a sulfonyl halide having an optionally substituted alkyl or phenyl group.

10 Claims, No Drawings

(56) References Cited

OTHER PUBLICATIONS

Jones et al., "Simple phosphinite-oxazoline ligands for asymmetric catalysis," *Tetrahedron Letters* 42, pp. 5553-55555 (2001).

Braga et al., "The facile synthesis of chiral oxazoline catalysts for the diethylzinc addition to aldehydes," *Tetrahedron: Asymmetry* 14, pp. 3291-3295 (2003).

Obrecht et al., "An Efficient Strategy to Orthogonally Protected (R)- and (S)-a-Methyl(alkyl)serine-Containing Peptides via a Novel Azlactone/Oxazoline Interconversion Reaction," *J. Org. Chem.*, pp. 4080-4086 (1196).

Onomura et al., 131st Annual Meeting of Pharmaceutical Society of Japan (Shizuoka) Happyo Yoshi, "Synthesis of Optically Active Oxazolines by Catalytic Asymmetric Desymmetrization", VIII-5-1 (iv), (Feb. 1, 2011).

Hong et al., "Enantioselective Formation of tert-Alkylamines by Desymmetrization of 2-Substituted Serinols," *Chemistry A European Journal*, vol. 14, No. 11, pp. 3290-3296 (2008).

METHOD FOR PRODUCING OPTICALLY ACTIVE COMPOUND OR SALT THEREOF

TECHNICAL FIELD

The present invention relates to a process for producing an optically active oxazoline or a salt thereof, which is useful as an intermediate for the synthesis of pharmaceuticals, agrochemicals, and various other chemicals, and also relates to an optically active oxazoline or a salt thereof produced by the process, and optical resolution of an oxazoline.

BACKGROUND ART

Since optically active oxazolines are useful as a building block or a chiral ligand for organic synthesis, various production processes have been examined. Known examples of such processes for producing optically activity oxazolines include the processes described in Non Patent Literature 1 to 3.

However, each of the above processes needs an optically active compound as a starting material. That is, there has been a problem of high starting material costs, leading to high product prices. In addition, since the above production processes need multiple steps, there have been problems of requirement for large-scale production equipment, time-consuming separation, and low yield.

CITATION LIST

Non Patent Literature

[NPL 1] G. Jones, C. J. Richards (2001) Tetrahedron Letters 42: 5553-5555
[NPL 2] A. L. Braga et al. (2003) Tetrahedron Asymmetry 14: 3291-3295
[NPL 3] Daniel Obrecht et al. (1996) J. Org. Chem. 61: 4080-4086

SUMMARY OF INVENTION

Technical Problem

A primary objective of the present invention is to provide a production process in which an optically active oxazoline is synthesized from an optically inactive compound as a starting compound with fewer production steps.

Solution to Problem

The present inventors have wholeheartedly carried out investigations in order to solve the above problems, and found that the above problems can be solved at a time by the chemical reaction shown below. The present inventors further conducted various examinations and completed the present invention.

That is, the present invention comprises the following [1] to [10].

[1] A process for producing an optically active compound represented by Formula (3):

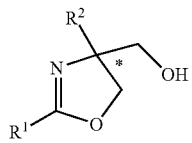

(3)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^2$ is a hydrogen atom or a group which is not involved in the reaction below; and * represents a chiral center) or a salt thereof by subjecting a compound represented by Formula (1):

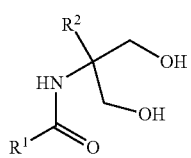

(1)

(wherein $R^1$ and $R^2$ have the same meanings as defined in Formula (3)) to a ring closure reaction in the presence of a chiral ligand having 1 or more coordination sites, a Lewis acid represented by Formula (2):

$$M_mZ_n \quad (2)$$

(wherein M is a metal ion, Z is a counter anion of M, and m and n are integers of 1 to 4), and a sulfonyl halide having an optionally substituted alkyl or phenyl group.

[2] The production process according to the above [1] wherein $R^1$ is an aryl group having 6 to 20 carbon atoms, a 5- to 8-membered monocyclic heteroaryl group or a polycyclic or condensed ring heteroaryl group, each heteroaryl group having 2 to 15 carbon atoms and at least one heteroatom, such as a nitrogen atom, an oxygen atom, and a sulfur atom, or a phenyl group substituted with an alkyl group, an alkenyl group, an alkoxy group, a halogen atom, a nitro group, or an aryl group.

[3] The production process according to the above [1] or [2] wherein $R^2$ is hydrogen or a hydrocarbon group.

[4] The production process according to any of the above [1] to [3] wherein $M_mZ_n$ is $Cu(OTf)_2$.

[5] The production process according to any of the above [1] to [4] wherein the reaction is performed in the presence of a base.

[6] The production process according to any of the above [1] to [5] wherein the reaction is performed in the presence of an organic solvent.

[7] An optically active compound represented by Formula (4):

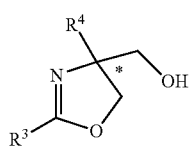

(4)

(wherein R³ is an aryl group having 6 to 20 carbon atoms, a 5- to 8-membered monocyclic heteroaryl group or a polycyclic or condensed ring heteroaryl group, each heteroaryl group having 2 to 15 carbon atoms and at least one heteroatom, such as a nitrogen atom, an oxygen atom, and a sulfur atom, or a phenyl group substituted with an alkyl group, an alkenyl group, an alkoxy group, a halogen atom, a nitro group, or an aryl group and R⁴ is a hydrogen atom or a group which is not involved in the reaction, excluding the case where R³ is a phenyl group and R⁴ is a hydrogen atom or a methyl group; and * represents a chiral center);

or Formula (4'):

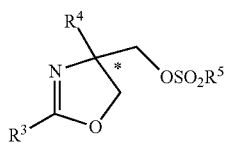

(4')

(wherein R³ and R⁴ have the same meanings as defined in the above (4); R⁵ is an optionally substituted alkyl or phenyl group; and * represents a chiral center) or a salt thereof.

[8] A process for producing, in an enantioselective manner, an (R) or (S) enantiomer of an optically active compound represented by Formula (3):

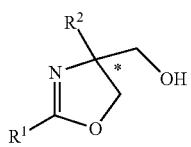

(3)

(wherein R¹ is an alkyl group, an alkynyl group, an alkenyl group, an aliphatic heterocyclic group, a cycloalkyl group, an aryl group, an aralkyl group, or an aromatic heterocyclic group, and any hydrogen atom of R¹ may be replaced with a substituent; R² is a hydrogen atom or a group which is not involved in the reaction below; and * represents a chiral center) or a salt thereof and an (R) or (S) enantiomer of an optically active compound represented by Formula (6):

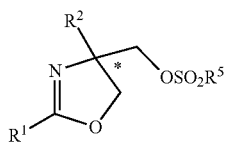

(6)

(wherein R¹ and R² have the same meanings as defined in Formula (3); R⁵ is an optionally substituted alkyl or phenyl group; and * represents a chiral center) or a salt thereof by subjecting a racemic mixture of a compound represented by Formula (5):

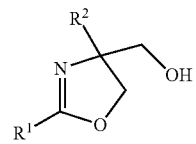

(5)

(wherein R¹ and R² have the same meanings as defined in Formula (3)) to a reaction in the presence of a chiral ligand having 1 or more coordination sites, a Lewis acid represented by Formula (2):

$$M_mZ_n \quad (2)$$

(wherein M is a metal ion, Z is a counter anion of M, and m and n are integers of 1 to 4), and a sulfonyl halide having an optionally substituted alkyl or phenyl group.

[9] A process for producing an optically active compound represented by Formula (8):

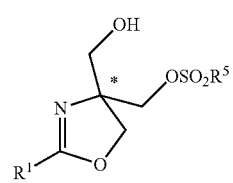

(8)

(wherein R¹ is an alkyl group, an alkynyl group, an alkenyl group, an aliphatic heterocyclic group, a cycloalkyl group, an aryl group, an aralkyl group, or an aromatic heterocyclic group, and any hydrogen atom of R¹ may be replaced with a substituent; R⁵ is an optionally substituted alkyl or phenyl group; and * represents a chiral center) or a salt thereof by subjecting a compound represented by Formula (7):

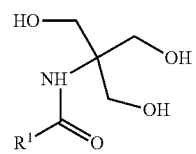

(7)

(wherein R¹ has the same meaning as defined in Formula (8)) to a reaction in the presence of a chiral ligand having 1 or more coordination sites, a Lewis acid represented by Formula (2):

$$M_mZ_n \quad (2)$$

(wherein M is a metal ion, Z is a counter anion of M, and m and n are integers of 1 to 4), and a sulfonyl halide having an optionally substituted alkyl or phenyl group.

[10] A process for producing an (R) or (S) enantiomer of an optically active compound represented by Formula (8):

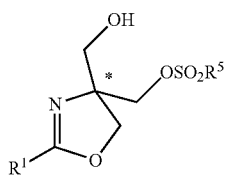

(8)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^5$ is an optionally substituted alkyl or phenyl group; and * represents a chiral center) or a salt thereof by subjecting a compound represented by Formula (9):

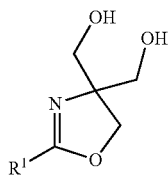

(9)

(wherein $R^1$ has the same meaning as defined in Formula (8)) to a reaction in the presence of a chiral ligand having 1 or more coordination sites, a Lewis acid represented by Formula (2):

$$MmZn \qquad (2)$$

(wherein M is a metal ion, Z is a counter anion of M, and m and n are integers of 1 to 4), and a sulfonyl halide having an optionally substituted alkyl or phenyl group.

Advantageous Effects of Invention

According to the present invention, an optically active compound represented by Formula (3) or Formula (4) or a salt thereof, which is an intermediate for the synthesis of various useful compounds, can be produced from an optically inactive compound as a starting compound with fewer production steps. In more detail, an optically active compound represented by Formula (3) or Formula (4) or a salt thereof can be produced from an optically inactive compound represented by Formula (1) as a starting compound in high yield and high optical purity. In addition, the present invention is industrially advantageous because asymmetric desymmetrization and ring formation by ring closure can be achieved simultaneously. Further, according to the present invention, a racemic mixture of a compound represented by Formula (5) as a starting material can be optically resolved in high yield and high optical purity. Further, according to the present invention, an optically active compound represented by Formula (8) or a salt thereof can be produced from an optically inactive compound represented by Formula (7) as a starting compound in high yield and high optical purity. Further, according to the present invention, an optically active compound represented by Formula (8) or a salt thereof can be produced from an optically inactive compound represented by Formula (9) as a starting material in high yield and high optical purity.

DESCRIPTION OF EMBODIMENTS

The present invention provides a production process in which an optically active oxazoline is synthesized from an optically inactive oxazoline, in particular a compound represented by Formula (3) or Formula (4) or a salt thereof, from an optically inactive compound as a starting compound with fewer production steps. The present invention also provides a process for optically resolving a racemic mixture of an oxazoline. The present invention also provides a production process in which a compound represented by Formula (8) or a salt thereof is synthesized.

Hereinafter, the process for producing a compound represented by Formula (3) or Formula (4) or a salt thereof, and the process for optically resolving a racemic mixture of an oxazoline will be described in detail.

Process for Producing Optically Active Oxazoline or Salt Thereof (1)

(Starting Compound)

The starting compound used in this aspect of the present invention is represented by Formula (1):

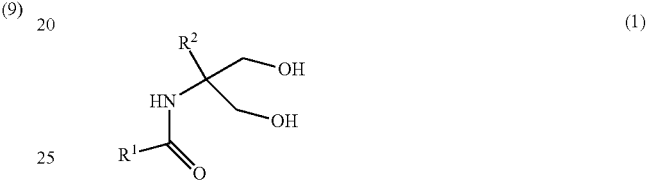

(1)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; and $R^2$ is a hydrogen atom or a group which is not involved in the reaction).

The alkyl group represented by $R^1$ may be a linear or branched alkyl group, for example, having 1 to 20 carbon atoms, such as methyl, ethyl, n-propyl, isopropyl, n-butyl, sec-butyl, isobutyl, tert-butyl, n-pentyl, neopentyl, tert-pentyl, isopentyl, 2-methylbutyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, heptyl, octyl, nonyl, decyl, cetyl, and stearyl. The number of carbon atoms in the above-mentioned alkyl group is preferably 1 to 12, and more preferably 1 to 6.

The alkynyl group represented by $R^1$ may be a linear or branched alkynyl group, for example, having 2 to 15 carbon atoms, preferably 2 to 10 carbon atoms, and more preferably 2 to 6 carbon atoms. Specific examples of the alkynyl group include ethynyl, 1-propynyl, 2-propynyl, 1-butynyl, 3-butynyl, pentynyl, and hexynyl.

The alkenyl group represented by $R^1$ may be a linear or branched alkenyl group, for example, having 2 to 15 carbon atoms, preferably 2 to 10 carbon atoms, and more preferably 2 to 6 carbon atoms. Specific examples of the alkenyl group include vinyl, 1-propenyl, allyl, 1-butenyl, 2-butenyl, 3-butenyl, pentenyl, hexenyl, isopropenyl, 2-methyl-2-propenyl, 1-methyl-2-propenyl, and 2-methyl-1-propenyl.

The aliphatic heterocyclic group represented by $R^1$ may be, for example, a 5- to 8-membered, preferably 5- or 6-membered, monocyclic aliphatic heterocyclic group or a polycyclic or condensed ring aliphatic heterocyclic group, each having 2 to 14 carbon atoms and at least one, preferably 1 to 3 heteroatoms, such as nitrogen, oxygen, and sulfur atoms. Examples of the aliphatic heterocyclic group include pyrrolidyl-2-one, piperidino, piperadinyl, morpholino, tetrahydrofuryl, tetrahydropyranyl, and tetrahydrothienyl.

The cycloalkyl group represented by $R^1$ may be a cycloalkyl group, for example, having 3 to 14 carbon atoms, preferably 5 to 12 carbon atoms, and more preferably 6 to 12 carbon atoms. Specific examples of the cycloalkyl group include cyclopropyl, cyclobutyl, cyclopentyl, methylcyclopentyl, cyclohexyl, cycloheptyl, cyclooctyl, 1,2-dimethylcyclopentyl, 1,3-dimethylcyclopentyl, and 1-ethyl-2-methylcyclopentyl.

The aryl group represented by $R^1$ may be, for example, an aryl group having 6 to 20 carbon atoms. Specific examples of the aryl group include phenyl, 1-naphthyl, 2-naphthyl, anthryl, phenanthryl, 2-biphenyl, 3-biphenyl, 4-biphenyl, and terphenyl.

The aralkyl group represented by $R^1$ may be a group derived from an alkyl group by replacing at least one hydrogen atom thereof with the above-mentioned aryl group. Specific examples of the aralkyl group include an aralkyl group having 7 to 18 carbon atoms, such as benzyl, phenethyl, 1-phenylpropyl, 3-naphthylpropyl, diphenylmethyl, 1-naphthylmethyl, 2-naphthylmethyl, 2,2-diphenylethyl, 3-phenylpropyl, 4-phenylbutyl, and 5-phenylpentyl.

The aromatic heterocyclic group represented by $R^1$ may be, for example, a 5- to 8-membered, preferably 5- or 6-membered, monocyclic heteroaryl group or a polycyclic or condensed ring heteroaryl group having 2 to 15 carbon atoms and at least one, preferably 1 to 3 heteroatoms, such as nitrogen, oxygen, and sulfur atoms. Specific examples of the 5- or 6-membered monocyclic heteroaryl or polycyclic or condensed ring heteroaryl group include furyl, thienyl, pyrrolyl, pyridyl, pyrimidinyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzoimidazolyl, benzoxazolyl, and benzothiazolyl.

Any hydrogen atom of the alkyl group, the alkynyl group, the alkenyl group, the aliphatic heterocyclic group, the cycloalkyl group, the aryl group, the aralkyl group, or the aromatic heterocyclic group may be replaced with a substituent. The substituent is not particularly limited, and examples thereof include an alkyl group, an alkynyl group, an alkenyl group, an aryl group, an aralkyl group, an alkoxy group, an alkylenedioxy group, an aryloxy group, an aralkyloxy group, a heteroaryloxy group, an alkylthio group, a cycloalkyl group, an aliphatic heterocyclic group, an aromatic heterocyclic group, an arylthio group, an aralkylthio group, a heteroarylthio group, an amino group, a substituted amino group, a cyano group, a hydroxyl group, an oxo group, a nitro group, a mercapto group, and a halogen atom. The number of the substituents is preferably 1 to 3, and more preferably 1 or 2.

The alkyl group as the substituent may be a linear or branched alkyl group, for example, having 1 to 20 carbon atoms. Specific examples thereof include the alkyl groups defined as $R^1$ above.

The alkynyl group as the substituent may be a linear or branched alkynyl group, for example, having 2 to 15 carbon atoms, preferably 2 to 10 carbon atoms, and more preferably 2 to 6 carbon atoms. Specific examples thereof include the alkynyl groups defined as $R^1$ above.

The alkenyl group as the substituent may be a linear or branched alkenyl group, for example, having 2 to 15 carbon atoms, preferably 2 to 10 carbon atoms, and more preferably 2 to 6 carbon atoms. Specific examples thereof include the alkenyl groups defined as $R^1$ above.

The aliphatic heterocyclic group as the substituent may be, for example, a 5- to 8-membered, preferably 5- or 6-membered, monocyclic heteroaryl group or a polycyclic or condensed ring aliphatic heterocyclic group, each heteroaryl group having 2 to 14 carbon atoms and at least one, preferably 1 to 3 heteroatoms, such as nitrogen, oxygen, and sulfur atoms. Specific examples thereof include the aliphatic heterocyclic groups defined as $R^1$ above.

The cycloalkyl group as the substituent may be, for example, a cycloalkyl group having 3 to 14 carbon atoms, preferably 5 to 12 carbon atoms, and more preferably 6 to 12 carbon atoms. Specific examples thereof include the cycloalkyl groups defined as $R^1$ above.

The aryl group as the substituent may be, for example, an aryl group having 6 to 20 carbon atoms. Specific examples thereof include the aryl groups defined as $R^1$ above.

The aryloxy group as the substituent may be, for example, an aryloxy group having 6 to 14 carbon atoms. Specific examples thereof include phenoxy, tolyloxy, xylyloxy, naphthoxy, and anthryloxy.

The aralkyl group as the substituent may be a group derived from an alkyl group by replacing at least one hydrogen atom thereof with the above-mentioned aryl group. Specific examples thereof include the aralkyl groups defined as $R^1$ above.

The aromatic heterocyclic group as the substituent may be, for example, a 5- to 8-membered, preferably 5- or 6-membered, monocyclic heteroaryl group or a polycyclic or condensed ring heteroaryl group, each heteroaryl group having 2 to 15 carbon atoms and at least one, preferably 1 to 3 heteroatoms, such as nitrogen, oxygen, and sulfur atoms. Specific examples thereof include the aromatic heterocyclic groups defined as $R^1$ above.

The alkoxy group as the substituent may be a linear, branched, or cyclic alkoxy group, for example, having 1 to 6 carbon atoms, and specific examples thereof include methoxy, ethoxy, n-propoxy, isopropoxy, n-butoxy, sec-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, cyclohexyloxy, methoxymethoxy, and 2-ethoxyethoxy.

The alkylenedioxy group as the substituent may be, for example, an alkylenedioxy group having 1 to 3 carbon atoms. Specific examples thereof include methylenedioxy, ethylenedioxy, trimethylenedioxy, propylenedioxy, and isopropylidenedioxy.

The alkylthio group as the substituent may be a linear, branched, or cyclic alkylthio group, for example, having 1 to 6 carbon atoms. Specific examples thereof include methylthio, ethylthio, n-propylthio, isopropylthio, n-butylthio, 2-butylthio, isobutylthio, tert-butylthio, pentylthio, hexylthio, and cyclohexylthio.

The aralkyloxy group as the substituent may be, for example, an aralkyloxy group having 7 to 12 carbon atoms. Specific examples thereof include benzyloxy, 1-phenylethoxy, 2-phenylethoxy, 1-phenylpropoxy, 2-phenylpropoxy, 3-phenylpropoxy, 1-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, and 6-phenylhexyloxy.

The arylthio group as the substituent may be, for example, an arylthio group having 6 to 14 carbon atoms. Specific examples thereof include phenylthio, tolylthio, xylylthio, and naphthylthio.

The heteroaryloxy group as the substituent may be, for example, a heteroaryloxy group having 2 to 14 carbon atoms and at least one, preferably 1 to 3 heteroatoms, such as nitrogen, oxygen, and sulfur atoms. Specific examples thereof include 2-pyridyloxy, 2-pyrazyloxy, 2-pyrimidyloxy, and 2-quinolyloxy.

The aralkylthio group as the substituent may be, for example, an aralkylthio group having 7 to 12 carbon atoms. Specific examples thereof include benzylthio and 2-phenethylthio.

The heteroarylthio group may be, for example, a heteroarylthio group having 2 to 14 carbon atoms and at least one, preferably 1 to 3 heteroatoms, such as nitrogen, oxygen, and sulfur atoms. Specific examples thereof include 2-pyridylthio, 4-pyridylthio, 2-benzimidazolylthio, 2-benzoxazolylthio, and 2-benzthiazolylthio.

The substituted amino group may be, for example, an amino group in which 1 or 2 hydrogen atoms are replaced with a substituent, such as an alkyl group, an aryl group, or an aralkyl group.

Examples of the amino group substituted with an alkyl group, i.e., an alkyl-substituted amino group, include a monoalkylamino or dialkylamino group, such as N-methylamino, N,N-dimethylamino, N,N-diethylamino, N,N-diisopropylamino, and N-cyclohexylamino.

Examples of the amino group substituted with an aryl group, i.e., an aryl-substituted amino group, include a monoarylamino or diarylamino group, such as N-phenylamino, N,N-diphenylamino, N,N-ditolylamino, N-naphthylamino, and N-naphthyl-N-phenylamino.

Examples of the amino group substituted with an aralkyl group, i.e., an aralkyl-substituted amino group, include a monoaralkylamino or diaralkylamino group, such as N-benzylamino and N,N-dibenzylamino.

In the above-mentioned substituents, 1 or more hydrogen atoms may be replaced with a halogen atom. Examples of the halogen atom include a fluorine atom, a chlorine atom, a bromine atom, and an iodine atom.

In the cases where the group represented by $R^1$ is a phenyl group substituted with a substituent, the substituent may be at any position of ortho, meta, and para. However, in view of reactivity and stereoselectivity, para-substitution is preferred. In the optionally substituted phenyl group represented by $R^1$, the number of hydrogen atoms replaced with a substituent may be one or more, but preferred is that only one hydrogen atom is replaced with a substituent.

$R^1$ is preferably an aryl group having 6 to 20 carbon atoms, a 5- to 8-membered monocyclic heteroaryl group or a polycyclic or condensed ring heteroaryl group, each heteroaryl group having 2 to 15 carbon atoms and at least one heteroatom, such as a nitrogen atom, an oxygen atom, and a sulfur atom, or a phenyl group substituted with alkyl, alkenyl, alkoxy, halogen, nitro, or aryl.

The group represented by $R^2$ which is not involved in the reaction may be any group as long as it is not involved in the reaction for producing the compound represented by the above (3) or (4), or a salt thereof. Preferred examples thereof include hydrocarbon groups, such as alkyl, aryl, aralkyl, alkenyl, and alkynyl. Specific examples of the alkyl, aryl, aralkyl, alkenyl, and alkynyl include those defined as $R^2$ above.

As the starting compound, commercial products may be used. Alternatively, the starting compound can be readily produced by a known process or a process equivalent thereto.

(Catalyst)

In the above ring closure reaction, a Lewis acid represented by Formula (2):

$$M_m Z_n \quad (2)$$

(wherein M is a metal ion, Z is a counter anion of M, and m and n are integers of 1 to 4) is used.

In Formula (2), the metal ion represented by M is not particularly limited, and examples thereof include representative metal ions, such as lithium, beryllium, aluminum, sodium, magnesium, potassium, calcium, strontium, barium, cesium, bismuth, gallium, cesium, and antimony; and transition metal ions, such as iron, copper, cobalt, nickel, mercury, palladium, zinc, silver, rhodium, platinum, scandium, yttrium, lanthanum, cerium, indium, ytterbium, and hafnium. Among them, preferred are transition metal ions; more preferred are an iron ion, a copper ion, a cobalt ion, a nickel ion, a copper ion, a zinc ion, a silver ion, a rhodium ion, a palladium ion, and a platinum ion; still more preferred are a copper ion and a zinc ion; and particularly preferred is a copper ion.

In Formula (2), the counter anion of M, which anion is represented by Z, is not particularly limited, and examples thereof include halogen ions, such as ions of fluorine, chlorine, bromine, and iodine, a trifluoromethylsulfonate ion ($^-$OTf), a boron tetrafluoride ion ($^-BF_4$), a phosphorus hexafluoride ion ($^-PF_6$), an antimony hexafluoride ion ($^-SbF_6$), a bis(trifluoromethylsulfonyl) imide ion ($^-NTf_2$), an acetate ion ($^-$OAc), and a trifluoroacetate ion ($^-OCOCF_3$). Among them, preferred as Z is a fluoride ion, a chloride ion, $^-$OTf, $^-BF_4$ or $^-PF_6$, and particularly preferred is $^-$OTf.

m and n are integers of 1 to 4, and each vary depending on the valence of M and the valence of Z so that the Lewis acid may be electrically neutral.

The Lewis acid represented by Formula (2) may be any combination of M and Z as above, and example of the Lewis acid include $Cu(OTf)_2$, $Zn(OTf)_2$, $CuBr_2$, $CuCl_2$, $CuF_2$, $Cu(BF_4)_2$, $Cu(PF_6)_2$, $Cu(SbF_6)_2$, $Cu(NTf_2)_2$, $PtCl_2$, $CoCl_2$, $PdCl_2$, $Pd(OAc)_2$, and $Pd(OCOCF_3)_2$. Among them, preferred are $Cu(OTf)_2$, $Zn(OTf)_2$, $CuCl_2$, $CuF_2$, $Cu(BF_4)_2$, $Cu(PF_6)_2$, $PtCl_2$, $CoCl_2$, $PdCl_2$, $Pd(OAc)_2$, and $Pd(OCOCF_3)_2$, and particularly preferred is $Cu(OTf)_2$.

The Lewis acid may be a commercial product, or a Lewis acid produced by a known process.

The amount of the Lewis acid is 0.001 to 1.00 mol, preferably 0.005 to 0.50 mol, and more preferably 0.01 to 0.20 mol relative to 1 mol of the compound represented by Formula (1).

The chiral ligand having 1 or more coordination sites which is used in the above ring closure reaction is not particularly limited. Examples thereof include an optically active diamine compound and an optically active oxazoline compound, and preferred is an optically active oxazoline compound.

Herein, a bisoxazoline compound is referred to as Box and includes a bisoxazoline compound in which each oxazoline ring has a phenyl group bound thereto (hereinafter Ph-Box), a bisoxazoline compound in which each oxazoline ring has an isopropyl group bound thereto (hereinafter i-Pr-Box), a bisoxazoline compound in which each oxazoline ring has a t-Bu bound thereto (hereinafter t-Bu-Box), and a bisoxazoline compound in which each oxazoline ring has a benzyl group bound thereto.

Examples of the optically active oxazoline compound include one in which the oxazoline rings have substituents with identical configurations, for example, (R,R)-Ph-Box having the structure of the following Formula (10):

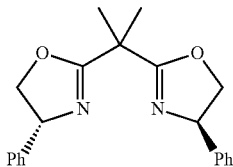

(10)

(S,S)-Ph-Box having the structure of the following Formula (11):

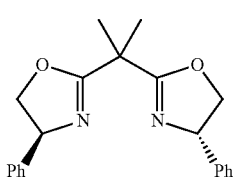

(11)

(R,R)-i-Pr-Box having the structure of the following Formula (12):

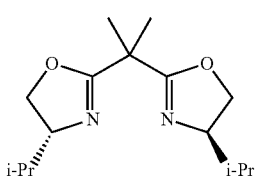

(12)

(S,S)-i-Pr-Box having the structure of the following Formula (13):

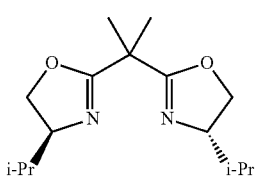

(13)

Among them, in view of the combination with the Lewis acid and of stereoselectivity, particularly preferred are (R,R)-Ph-Box and (S,S)-Ph-Box.

The chiral ligand preferably has 2 or more coordination sites. The amount of the chiral ligand is 0.001 to 1.00 mol, preferably 0.005 to 0.50 mol, and more preferably 0.01 to 0.20 mol relative to 1 mol of the compound represented by Formula (1).

The optically active bisoxazoline compound may be a commercial product. Alternatively, the optically active bisoxazoline compound may be produced by a process known per se. Such a process is described in, for example, J. Am. Chem. Soc., 113, 728-729 (1991).

In the present invention, the chiral ligand and the Lewis acid form a metal complex as a result of coordinate bonding, and serve as a catalyst in the production of the optically active compound.

In this aspect of the present invention, a sulfonyl halide having an optionally substituted alkyl or phenyl group is used. The optionally substituted phenyl group may be a phenyl group or a group derived from a phenyl group by replacing any hydrogen atom thereof with a substituent. Specific examples of the phenyl group in the sulfonyl halide having an optionally substituted alkyl or phenyl group include a phenyl group and a group derived from a phenyl group by replacing any hydrogen atom thereof with a substituent represented by R'. Among them, preferred are alkylphenyl groups having 1 to 4 carbon atoms, such as p-methylphenyl, p-ethylphenyl, p-propylphenyl, p-isopropylphenyl, and p-butylphenyl; alkoxyphenyl groups having 1 to 4 carbon atoms, such as p-methoxyphenyl, p-ethoxyphenyl, p-isopropoxyphenyl, and p-n-butoxyphenyl; halophenyl groups, such as p-fluorophenyl, p-chlorophenyl, p-bromophenyl, and p-iodophenyl; p-carbamoylphenyl; p-acylaminophenyl; p-amidophenyl; and p-nitrophenyl, and particularly preferred are p-methylphenyl, p-chlorophenyl, p-methoxyphenyl, and p-nitrophenyl.

In the optionally substituted phenyl group, the number of hydrogen atoms replaced with a substituent may be one or more, but preferred is that only one hydrogen atom is replaced with a substituent. In the optionally substituted phenyl group, the substitution site is not particularly limited, and the substituent may be at any position of ortho, meta, and para. However, in view of reactivity and stereoselectivity, para-substitution is preferred.

The optionally substituted alkyl group may be a linear or branched alkyl group, for example having 1 to 20 carbon atoms, or a group derived from the alkyl group by replacing any hydrogen atom with a substituent. Specific examples of the linear or branched alkyl group include linear or branched alkyl groups, such as methyl, ethyl, n-propyl, isopropyl, n-butyl, sec-butyl, isobutyl, tert-butyl, n-pentyl, neopentyl, tert-pentyl, isopentyl, 2-methylbutyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, heptyl, octyl, nonyl, decyl, cetyl, and stearyl. The optionally substituted alkyl group preferably has 1 to 4 carbon atoms, and more preferably is methyl or ethyl.

In the optionally substituted alkyl group, 1 or more hydrogen atoms may be replaced with a substituent. In the optionally substituted alkyl group, the substitution site is not particularly limited. As the substituent, those shown as exemplary substituents in the above (1) may be used.

The halogen atom in the sulfonyl halide is not particularly limited, and examples thereof include a fluorine atom, a chlorine atom, a bromine atom, and an iodine atom. Among them, preferred are a chlorine atom and a bromine atom, and particularly preferred is a chlorine atom.

The amount of the sulfonyl halide is 0.1 to 10 mol, preferably 0.5 to 5.0 mol, and particularly preferably 0.8 to 4.0 mol relative to 1 mol of the starting compound represented by Formula (1).

By using the above catalyst in combination, an optically active target compound can be produced from an optically inactive compound as a starting compound in high yield and high optical purity.

The catalyst may be a homogeneous catalyst or a heterogeneous catalyst. The catalyst may be produced by a publicly known process. Alternatively, a commercially available catalyst may be used. In addition to the above catalyst, another publicly known catalyst may be used.

(Solvent)

The solvent for the above-mentioned reaction is not particularly limited, and an organic or inorganic solvent may be used.

Examples of the organic solvent include aliphatic hydrocarbons such as pentane, hexane, heptane, octane, and cyclohexane; aromatic hydrocarbons such as benzene, toluene, and xylene; halohydrocarbons such as dichloromethane, 1,2-dichloroethane, chloroform, tetrachlorocarbon, and o-dichlorobenzene; alcohols, such as methanol, ethanol, isopropyl alcohol, t-butyl alcohol, and t-amylalcohol; ethers such as dimethyl ether, ethylmethyl ether, diethyl ether, diisopropyl ether, diglyme, tert-butyl methyl ether, dimethoxyethane, ethylene glycol diethyl ether, tetrahydrofuran, and 1,4-dioxane; amides such as N,N-dimethylformamide, N,N-dimethylacetamide, and N-methylpyrrolidone; sulfoxides, such as dimethyl sulfoxide; nitriles, such as acetonitrile, propionitrile, and benzonitrile; ketones, such as acetone, methyl ethyl ketone, and methyl isobutyl ketone; and ester compounds, such as methyl acetate and ethyl acetate.

Examples of the inorganic solvent include acidic aqueous solutions, such as hydrochloric acid, sulfuric acid, nitric acid, carbonic acid, and phosphoric acid; basic aqueous solutions, such as sodium hydroxide, magnesium hydroxide, calcium hydroxide, potassium hydroxide, and sodium hydrogen carbonate; and neutral aqueous solutions, such as pure water and brine.

Organic solvents are preferred, and among them, particularly preferred are acetonitrile, propionitrile, dichloromethane, toluene, ethyl acetate, tetrahydrofuran, diethylether, dioxane, diglyme, N,N-dimethylformamide, methanol, ethanol, isopropanol, t-butanol, t-amylalcohol, and methylisobutylketone.

The solvents may be used alone or in combination of two or more kinds thereof. The amount of the solvent is not particularly limited as long as it is excessive relative to that of the starting material, and may be, for example, 0.1 to 100 parts by weight relative to 1 part by weight of the starting material represented by Formula (1).

(Base)

Preferred examples of the base that may be used for the reaction include inorganic bases, such as, sodium hydroxide, potassium hydroxide, potassium carbonate, sodium carbonate, cesium carbonate, and ammonia; and organic bases, such as, triethylamine, diisopropylethylamine, and pyridine. The amount of the base is 0.1 to 10 mol, preferably 0.5 to 8.0 mol, and particularly preferably 0.8 to 5.0 mol relative to 1 mol of the starting compound represented by Formula (1).

(Reaction)

The reaction of this aspect of the present invention is performed by subjecting a compound represented by the above Formula (1) to a ring closure reaction in the presence of a chiral ligand having 1 or more coordination sites, a Lewis acid represented by Formula (2):

$$M_mZ_n \tag{2}$$

(wherein M is a metal ion, Z is a counter anion of M, and m and n are integers of 1 to 4), and a sulfonyl halide having an optionally substituted alkyl or phenyl group to give a compound represented by Formula (3):

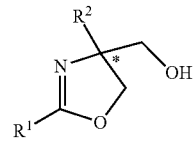

(3)

(wherein $R^1$ and $R^2$ have the same meanings as defined above, and * represents a chiral center) or a salt thereof.

The above reaction readily occurs in two steps. In the cases where the sulfonyl halide having an optionally substituted alkyl or phenyl group in the above reaction is p-toluenesulfonyl halide, the intermediate product through which the reaction proceeds is a compound of Formula (14):

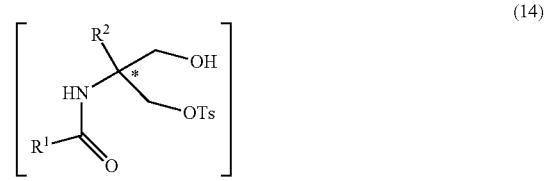

(14)

(wherein $R^1$ and $R^2$ have the same meanings as defined above, and * represents a chiral center) which is produced as a result of asymmetric desymmetrization.

According to the present invention, an optically active compound can be produced from an optically inactive compound as a starting compound. That is, since a cheap compound not having optical activity can be used instead of an expensive compound having optical activity as a starting compound, the production cost can be reduced. In addition, since asymmetric desymmetrization and ring formation by ring closure can be achieved simultaneously, the following advantages are brought about: the number of processing steps can be reduced; the synthesis of an optically active compound can be performed using a smaller-scale production equipment; the time and effort for separating the compound can be saved; and the reduction in yield due to separation processes can be prevented.

Further, since the above reaction can produce an optically active oxazoline compound represented by Formula (3) or (4) or a salt thereof through ring closure of a non-cyclic compound represented by Formula (1), the present invention can be used for the production of various useful compounds.

In the above reaction, the optical activity of the produced oxazoline compound (Formula (3)) depends on the stereoselectivity of the above-mentioned chiral ligand. For example, when (R,R)-Ph-Box is used as the above-mentioned chiral ligand, the (R) enantiomer of the oxazoline compound is preferentially produced as compared with the (S) enantiomer. Here, it is assumed that the (S) enantiomer of the oxazoline compound is also once produced in a certain amount. However, it is assumed that, under the reaction conditions of the present invention, as shown in the optical resolution of an oxazoline described later, since the hydrogen atom of the hydroxyl group in the (S) enantiomer is converted to a group corresponding to the sulfonyl halide used, i.e., a sulfonyl group derived from the sulfonyl halide by removing the halogen atom (for example, when p-toluenesulfonyl chloride is used as the sulfonyl halide, the hydrogen atom of the hydroxyl group in the (S) enantiomer is converted to a p-toluenesulfonyl group (-Ts)), the amount of the (S) enantiomer of the oxazoline compound having a hydroxyl group is further reduced, resulting in a higher stereoselectivity of the (R) enantiomer.

The oxazoline compound in which a sulfonyloxy group has been introduced is indicated as an (R) enantiomer in terms of notation, but the configuration of the chiral carbon remains the same as that of the (S) enantiomer of the oxazoline compound having a hydroxyl group.

Herein, "optically active" means that the compound is not a mixture of equal amounts of enantiomers having different chiral carbon configurations (for example, a racemic mixture), and a compound in which one of the enantiomers exists in an excess amount is defined as "optically active".

(Reaction Conditions)

The reaction temperature for the reaction is not particularly limited. The reaction can be performed under the condition of −20 to 80° C., and preferred is 5 to 40° C. The pressure for the reaction is not particularly limited, and may be any of reduced pressure, atmospheric pressure, and increased pressure. For example, 0.1 to 20 Pa is allowable, but 0.7 to 1.2 Pa is preferred.

The reaction can be advanced at ordinary temperatures and ordinary pressures, and therefore, the production equipment can be simplified, which contributes to reduction in production cost.

The duration of the above reaction is not particularly limited. For example, 5 minutes to 72 hours is allowable, and 10 minutes to 48 hours is preferred.

The reaction can be advanced preferably by mixing the above-mentioned starting material with other components under stirring.

(Product)

The target compound produced by the reaction is represented by Formula (3):

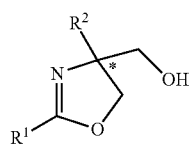

(3)

(wherein $R^1$ and $R^2$ have the same meanings as defined above, and * represents a chiral center), and more preferably represented by Formula (4):

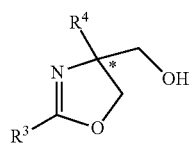

(4)

(wherein $R^3$ is an aryl group having 6 to 20 carbon atoms, a 5- to 8-membered monocyclic heteroaryl group or a polycyclic or condensed ring heteroaryl group, each heteroaryl group having 2 to 15 carbon atoms and at least one heteroatom, such as a nitrogen atom, an oxygen atom, and a sulfur atom, or a phenyl group substituted with an alkyl group, an alkenyl group, an alkoxy group, a halogen atom, a nitro group, or an aryl group and $R^4$ is a hydrogen atom or a group which is not involved in the reaction, excluding the case where $R^3$ is a phenyl group and $R^4$ is a hydrogen atom or a methyl group; and * represents a chiral center).

The aryl group having 6 to 20 carbon atoms represented by $R^3$ may be, for example, phenyl, 1-naphthyl, 2-naphthyl, anthryl, phenanthryl, 2-biphenyl, 3-biphenyl, 4-biphenyl, and terphenyl.

Specific examples of the 5- to 8-membered monocyclic heteroaryl group or a polycyclic or condensed ring heteroaryl group, each heteroaryl group having 2 to 15 carbon atoms and at least one heteroatom such as nitrogen, oxygen, and sulfur atoms, represented by $R^3$ include furyl, thienyl, pyrrolyl, pyridyl, pyrimidinyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzoimidazolyl, benzoxazolyl, and benzothiazolyl.

Specific examples of the alkyl group as the substituent, the alkenyl group as the substituent, the alkoxy group as the substituent, the halogen atom as the substituent, the nitro group as the substituent, and the aryl group as the substituent include those mentioned for $R^1$ above.

The group represented by $R^4$ in Formula (4) which is not reactive in the reaction may be any group as long as it is not reactive in the reaction for producing the compound represented by the above (4) or a salt thereof. Preferred examples thereof include hydrocarbon groups, such as alkyl, aryl, and alkenyl. Specific examples of the alkyl, aryl, and alkenyl include those mentioned for $R^1$ above.

Specific examples of the compound represented by Formula (4) include those represented by Formula (3). However, the cases where $R^1$ is a phenyl group and $R^2$ is a hydrogen atom or a methyl group are excluded.

The target compound represented by Formula (3) or (4) may be obtained as the compound itself or as a salt. The salt comprising the compound is not particularly limited as long as an ion derived from the target compound is ionically bonded to a counter ion, and specific examples of the salt include pharmaceutically acceptable salts, for example, inorganic salts, such as a sodium salt, a potassium salt, a magnesium salt, and a calcium salt; organic salts, such as angelic acid, lysine, ethanolamine, and N,N'-dibenzylethylenediamine; triterpene alcohol; and plant sterols.

(Separation of Reactant)

The target compound represented by Formula (3) or (4), which is produced by the reaction, may be isolated or purified, or used as a synthetic intermediate without isolation or purification, and subjected to the next reaction. The isolation or purification is performed by a publicly known method. Examples of such a known method include distillation, concentration, extraction, crystallization, chromatography, filtration, dialysis, and centrifugation.

(Use of Product)

The target compound represented by Formula (3) or (4) is used for various purposes, such as medical, industrial, and agricultural purposes. Examples of the specific use include a synthetic intermediate used for the synthesis of a useful compound. For example, the target compound can be used as a building block for non-natural amino acid synthesis.

The target compound may be used alone or as a mixture of two or more compounds. The target compound may be used in any state of solid, liquid, and gas.

(By-Product)

The above reaction produces a compound represented by Formula (6):

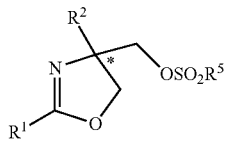

(6)

(wherein $R^1$ and $R^2$ have the same meanings as defined in the above (1); $R^5$ is an optionally substituted alkyl or phenyl group; and * represents a chiral center)
and preferably represented by Formula (4'):

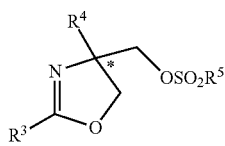

(4')

(wherein $R^3$ and $R^4$ have the same meanings as defined in the above (4); $R^5$ has the same meanings as defined in the above (6); and * represents a chiral center) or a salt thereof.

Specific examples of $R^1$ and $R^2$ in Formula (6) include those mentioned for Formula (1) above.

The alkyl group represented by $R^5$ in Formula (6) may be a linear or branched alkyl group, for example, having 1 to 20 carbon atoms, and specific examples thereof include those mentioned for $R^1$ above.

The substituent in the alkyl or phenyl group represented by $R^5$ in Formula (6) may be, for example, an alkyl group, an alkynyl group, an alkenyl group, an aryl group, an alkoxy group, an alkylenedioxy group, an aryloxy group, an aralkyloxy group, a heteroaryloxy group, an alkylthio group, a cycloalkyl group, an aliphatic heterocyclic group, an arylthio group, an aralkylthio group, a heteroarylthio group, an amino group, a substituted amino group, a cyano group, a hydroxyl group, an oxo group, a nitro group, a mercapto group, and a halogen atom. Specific examples thereof include those mentioned as the substituent in the above $R^1$.

Specific examples of $R^3$ and $R^4$ in Formula (4') include those mentioned for Formula (4) above.

$R^5$ in Formula (4') has the same meaning as in Formula (6).

The compound represented by Formula (6) or Formula (4') may be made into an optically active oxazoline compound by hydrolysis of the sulfonyloxy group. Alternatively, the compound may be made into a synthetic intermediate used for the synthesis of a useful compound, by converting the sulfonyloxy group into an azido group, a cyano group, an amino group, etc.

The target compound represented by Formula (6) or (4') may be obtained as the compound itself or as a salt. The salt comprising the compound is not particularly limited as long as an ion derived from the target compound is ionically bonded to a counter ion, and specific examples of the salt include pharmaceutically acceptable salts, for example, inorganic salts, such as a sodium salt, a potassium salt, a magnesium salt, and a calcium salt; organic salts, such as angelic acid, lysine, ethanolamine, and N,N'-dibenzylethylenediamine; triterpene alcohol; and plant sterols.

The compound represented by Formula (6) or (4') may be isolated or purified, or used as a synthetic intermediate without isolation or purification, and subjected to the next reaction. The isolation or purification is performed by a publicly known method. Examples of such a known method include distillation, concentration, extraction, crystallization, chromatography, filtration, dialysis, and centrifugation.

The compound represented by Formula (6) or (4') is used for various purposes, such as medical, industrial, and agricultural purposes. Specific examples of the use include a synthetic intermediate used for the synthesis of a useful compound. In this case, the compound may be made into an optically active oxazoline compound by hydrolysis of the sulfonyloxy group and used as a building block for non-natural amino acid synthesis. Alternatively, the compound may be made into a synthetic intermediate used for the synthesis of a useful compound, by converting the sulfonyloxy group into an azido group, a cyano group, an amino group, etc.

The compound represented by Formula (6) or (4') may be used alone or as a mixture of two or more compounds. The target compound may be used in any state of solid, liquid, and gas.

Optical Resolution of Oxazoline
(Starting Compound)

The starting compound used in this aspect of the present invention is a racemic mixture of the compound represented by Formula (5):

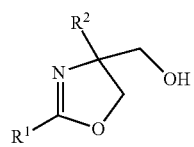

(5)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; and $R^2$ is a hydrogen atom or a group which is not reactive in the reaction).

$R^1$ and $R^2$ in the compound represented by Formula (5) have the same meaning as in Formula (1). The starting compound is a racemic mixture (a mixture of equal amounts of a pair of enantiomers having chemical structures that are mirror images of each other) and therefore is not optically active.

(Catalyst)

In the optical resolution, a Lewis acid represented by Formula (2):

$$M_mZ_n \qquad (2)$$

(wherein M is a metal ion, Z is a counter anion of M, and m and n are integers of 1 to 4) is used. Examples of the metal ion represented by M, the counter anion of M represented by Z, and the Lewis acid include those used in the production of the optically active oxazoline or a salt thereof.

The amount of the Lewis acid is 0.001 to 1.00 mol, preferably 0.005 to 0.50 mol, and more preferably 0.01 to 0.20 mol relative to 1 mol of the compound represented by Formula (5).

Examples of the chiral ligand having 1 or more coordination sites used in the optical resolution include those used in the production of the optically active oxazoline or a salt thereof.

The amount of the chiral ligand is 0.001 to 1.00 mol, preferably 0.005 to 0.50 mol, and more preferably 0.01 to 0.20 mol relative to 1 mol of the compound represented by Formula (5).

Examples of the sulfonyl halide having an optionally substituted alkyl or phenyl group used in the optical resolution include those used in the production of the optically active oxazoline or a salt thereof.

The amount of the sulfonyl halide is 0.1 to 10 mol, preferably 0.3 to 5.0 mol, and particularly preferably 0.5 to 3.0 mol relative to 1 mol of the starting material represented by Formula (5).

(Solvent)

The solvent for the above-mentioned reaction is not particularly limited, and an organic or inorganic solvent may be used, and examples thereof include those used in the production of the optically active oxazoline or a salt thereof.

The amount of the solvent is not particularly limited as long as it is excessive relative to that of the starting material, and may be, for example, 0.1 to 100 parts by weight relative to 1 part by weight of the starting material represented by Formula (5).

(Base)

Examples of the base that may be used in the reaction include those used in the production of the optically active oxazoline or a salt thereof.

The amount of the base is 0.1 to 10 mol, preferably 0.3 to 8.0 mol, and particularly preferably 0.5 to 5.0 mol relative to 1 mol of the starting material represented by Formula (5).

(Reaction)

In this aspect of the present invention, a racemic mixture of a compound represented by Formula (5) is subjected to a reaction in the presence of a chiral ligand having 1 or more coordination sites, a Lewis acid represented by Formula (2):

$$M_mZ_n \quad (2)$$

(wherein M is a metal ion, Z is a counter anion of M, and m and n are integers of 1 to 4), and a sulfonyl halide having an optionally substituted alkyl or phenyl group, and thereby the compound is optically resolved to give the (R) enantiomer or the (S) enantiomer of an optically active compound represented by Formula (3):

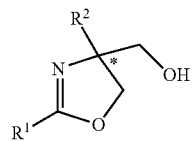

(3)

(wherein $R^1$ and $R^2$ have the same meanings as defined in Formula (5), and * represents a chiral center) or a salt thereof, and the (R) enantiomer or the (S) enantiomer of an optically active compound represented by Formula (6):

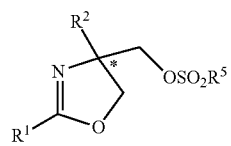

(6)

(wherein $R^1$ and $R^2$ have the same meanings as defined in Formula (5); $R^5$ is an optionally substituted alkyl or phenyl group; and * represents a chiral center) or a salt thereof.

According to this aspect of the present invention, a racemic mixture of a compound represented by Formula (5) as a starting material can be optically resolved into the (R) enantiomer or the (S) enantiomer of an optically active compound represented by Formula (3) and the (R) enantiomer or the (S) enantiomer of an optically active compound represented by Formula (6).

In the above reaction, the optical activity of the produced oxazoline compound (Formula (3)) depends on the stereoselectivity of the above-mentioned chiral ligand.

For example, when (R,R)-Ph-Box is used as the above-mentioned chiral ligand, the (R) enantiomer of the oxazoline compound represented by Formula (3) is produced. Here, since the hydrogen atom of the hydroxyl group in the (S) enantiomer of the oxazoline compound represented by Formula (3) is converted to a group corresponding to the sulfonyl halide used, i.e., a sulfonyl group derived from the sulfonyl halide by removing the halogen atom, the amount of the (S) enantiomer of the oxazoline compound represented by Formula (3) is reduced, resulting in a higher stereoselectivity of the (R) enantiomer.

The oxazoline compound of Formula (6) in which a sulfonyloxy group has been introduced is indicated as an (R) enantiomer in terms of notation, but the configuration of the chiral carbon remains the same as that of the (S) enantiomer of the oxazoline compound represented by Formula (3).

Examples of the reaction conditions, separation of reactant, and use of product include those described in the process for producing optically active oxazoline or salt thereof (1).

Process for Producing Optically Active Oxazoline or Salt Thereof (2)

The present invention includes a process for producing an optically active compound represented by Formula (8):

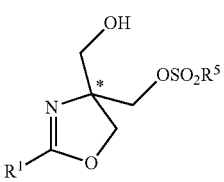

(8)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^5$ is an optionally substituted alkyl or phenyl group; and * represents a chiral center) or a salt thereof by subjecting a compound represented by Formula (7):

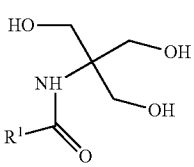

(7)

(wherein $R^1$ has the same meaning as defined in the above (8)) to a reaction in the presence of a chiral ligand having 1 or more coordination sites, a Lewis acid represented by Formula (2):

$$MmZn \quad (2)$$

(wherein M is a metal ion, Z is a counter anion of M, and m and n are integers of 1 to 4), and a sulfonyl halide having an optionally substituted alkyl or phenyl group.
(Starting Compound)

In this aspect of the present invention, a compound represented by Formula (7) is used as a starting compound. Examples of $R^1$ in Formula (7) include those described regarding Formula (1) in the process for producing optically active oxazoline or salt thereof (1).

The Lewis acid, the examples of the chiral ligand, the production process, the amounts, etc. are the same as those described in the process for producing optically active oxazoline or salt thereof (1).

Examples of the solvent include those described regarding the process for producing optically active oxazoline or salt thereof (1), but particularly preferred is MeCN (acetonitrile).

Examples of the base include those described regarding the process for producing optically active oxazoline or salt thereof (1), but particularly preferred is $K_2CO_3$ or $Na_2CO_3$. The amount of the base is 0.2 to 20 mol, preferably 1.0 to 16.0 mol, and particularly preferably 1.6 to 10.0 mol relative to 1 mol of the starting material represented by Formula (7).

Examples of the sulfonyl halide having an optionally substituted alkyl or phenyl group include those described in the process for producing optically active oxazoline or salt thereof (1). Among them, particularly preferred is a phenyl sulfonyl halide or a phenyl sulfonyl halide substituted with an alkyl group or a halogen atom at position 4. The amount of the sulfonyl halide is 0.2 to 20 mol, preferably 1.0 to 10.0 mol, and particularly preferably 1.6 to 8.0 mol relative to 1 mol of the starting material represented by Formula (7).

The duration of the above reaction is not particularly limited. For example, 5 minutes to 96 hours is allowable, and 10 minutes to 72 hours is preferred.
(Product)

In the reaction, an optically active compound represented by Formula (8) or a salt thereof is obtained as a product. Examples of $R^1$ in Formula (8) include those of Formula (7), and examples of $R^5$ include those described regarding Formula (6) in the process for producing optically active oxazoline or salt thereof (1).
(By-Product)

In the reaction, a compound represented by Formula (15):

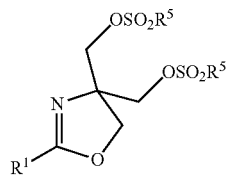

(15)

(wherein $R^1$ and $R^5$ have the same meanings as defined in Formula (8)) or a salt thereof is obtained as a by-product.
(Reaction)

According to this aspect of the present invention, an optically active compound represented by Formula (8) can be produced from a compound represented by Formula (7), which is inexpensive and readily available, as a starting compound.

Specifically, sulfonylation of one hydroxyl group of the starting compound leads to a ring closure reaction to form an oxazoline ring, thereby producing an intermediate product represented by the following Formula (9):

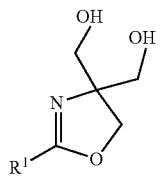

(9)

Then, the hydrogen atom of one hydroxyl group of the intermediate product is stereoselectively replaced with a group derived from the sulfonyl halide used (i.e., a sulfonyl group derived from the sulfonyl halide by removing the halogen atom). Thus the optically active oxazoline compound represented by Formula (8) is produced.

Process for Producing Optically Active Oxazoline or Salt Thereof (3)

One aspect of the present invention is a process for producing an (R) or (S) enantiomer of an optically active compound represented by Formula (8):

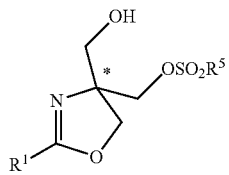

(8)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^5$ is an optionally substituted alkyl or phenyl group; and * represents a chiral center) or a salt thereof by subjecting a compound represented by Formula (9):

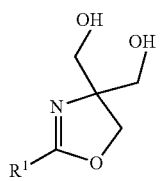

(9)

(wherein $R^1$ has the same meaning as defined in Formula (8)) to a reaction in the presence of a chiral ligand having 1 or more coordination sites, a Lewis acid represented by Formula (2):

$$MmZn \quad (2)$$

(wherein M is a metal ion, Z is a counter anion of M, and m and n are integers of 1 to 4), and a sulfonyl halide having an optionally substituted alkyl or phenyl group.
(Starting compound) In this aspect of the present invention, a compound represented by Formula (9) is used as a starting compound. Examples of $R^1$ in Formula (9) include those described regarding Formula (1) in the process for producing optically active oxazoline or salt thereof (1).

The Lewis acid, the examples of the chiral ligand, the production process, the amounts, etc. are the same as those described in the process for producing optically active oxazoline or salt thereof (1).

The types of the solvent, the base, the sulfonyl halide having an optionally substituted alkyl or phenyl group, and the reaction duration are the same as those described in the process for producing optically active oxazoline or salt thereof (2).

(Product)

In the reaction, an optically active compound represented by Formula (8) or a salt thereof is obtained as a product. Examples of $R^1$ in Formula (8) include those of Formula (7), and examples of $R^5$ include those described regarding Formula (6) in the process for producing optically active oxazoline or salt thereof (1).

(By-Product)

In the reaction, a compound represented by Formula (15):

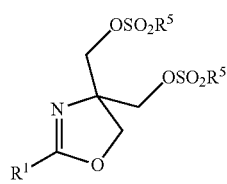

(15)

(wherein $R^1$ and $R^5$ have the same meanings as defined in Formula (8)) or a salt thereof is obtained as a by-product.

(Reaction)

According to this aspect of the present invention, an optically active compound represented by Formula (8) can be produced from a compound represented by Formula (9) as a starting compound.

EXAMPLES

Hereinafter, the present invention will be more specifically illustrated by Examples, but the present invention is not limited thereto. In Examples, physical properties were measured under the following conditions.

(Measurement Conditions)

The melting point was measured using "MICRO MELTING POINT APPARATUS" made by Yanaco. The measured values shown are all unadjusted values.

The infrared absorption spectrum (IR) was measured using "FTIR-8400S" made by Shimadzu Corp.

The nuclear magnetic resonance spectrum (NMR) was measured using "VARIAN Gemini-300 (300 MHz)". The measurement was performed using TMS (tetramethylsilane) as an internal standard substance and $CDCl_3$ as a solvent at room temperature. The measured values are all shown in δ values (ppm).

The optical rotation was measured using "DIP-1000" made by Jasco Corp.

High performance liquid chromatography (HPLC) was performed using "LC-20AT" made by Shimadzu Corp. (pump), "SPD-20A" made by Shimadzu Corp. (UV detector), "C-R8A CHROMATOPAC" (recorder), and "CHIRALPAC" series made by Daicel Chemical Industries, Ltd. (optically active column). The optical purity was determined based on the differences in the retention time in HPLC.

The mass spectrum (MS) was measured using "JMS-700N" made by JEOL Ltd.

Column chromatography was performed using "Silica Gel 60, spherical, neutrality" made by Nacalai Tesque, Inc.

The solvents and reagents used for the reactions were commercial products unless otherwise stated. For drying the extraction solvent, anhydrous sodium sulfate was used.

Example 1

Production of Optically Active Oxazoline Compound (1)

This experiment was conducted at ordinary temperature and pressure. In 2 mL of tert-butanol, 0.1 mmol of $Cu(OTf)_2$ and 0.1 mmol of (R,R)-Ph-Box were mixed and stirred for 10 minutes. To this, 0.5 mmol of a compound having the structure of the following formula:

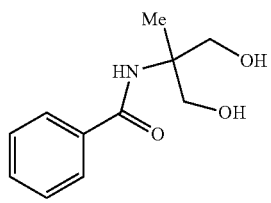 [SMILES: CC(CO)(CO)NC(=O)c1ccccc1]

was added as a starting material.

Then, 1.5 mmol of potassium carbonate was added thereto and finally 1 mmol of p-toluenesulfonyl chloride was added, and the mixture was stirred for 12 hours. After the reaction, water was added and extraction with ethyl acetate was performed 3 times. The organic layer was dried over anhydrous sodium sulfate and filtered, and then the solvent was evaporated off under reduced pressure. The residue was purified by column chromatography (eluent: n-hexane/ethyl acetate=3/1 (v/v)) to give (+)-4,5-dihydro-4-hydroxymethyl-4-methyl-2-phenyloxazole. The yield was 85%. The optical purity was 95% ee (R enantiomer).

The structure and the physical property data of the optically active oxazoline compound obtained by the above reaction are shown below.

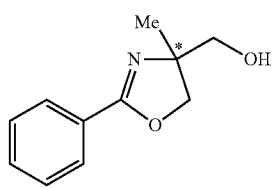 [SMILES: CC1(CO)COC(c2ccccc2)=N1]

white crystal; m.p. 102-104° C.;

$[\alpha]_D^{16}$=+15.2 (c 0.10, $CHCl_3$);

IR (neat): v=3171 (br), 2972, 2895, 2862, 1641, 1076 $cm^{-1}$;

$^1$H-NMR ($CDCl_3$): δ=1.32 (s, 3H), 3.49 (d, J=11.4 Hz, 1H), 3.78 (d, J=11.1 Hz, 1H), 4.09 (d, J=8.1 Hz, 1H), 4.47 (d, J=8.4 Hz, 1H), 7.33-7.41 (m, 2H), 7.43-7.50 (m, 1H), 7.84-7.91 (m, 2H);

$^{13}$C-NMR (400 MHz, $CDCl_3$): δ=164.1, 131.2, 128.2, 128.0, 127.1, 74.5, 71.9, 67.8, 23.7;

HPLC: OD-H column (4.6 mmφ, 250 mm), n-Hexane: Isopropanol=10:1, wavelength: 254 nm, flow rate: 0.5 mL/min, retention time: 15.3 min, 26.9 min, 95% ee;

HRMS (M+H, FAB): m/z calcd for $C_{11}H_{14}NO_2$: 191.1024. found: 191.1038.

Example 2

The experiment was conducted in the same manner as in Example 1 except that position 4 of the phenyl group in the starting material was substituted with a methyl group to give (+)-4,5-dihydro-4-hydroxymethyl-4-methyl-2-(4-methylphenyl)oxazole. The yield was 89%. The optical purity was 94% ee ((+)-form).

The structure and the physical property data of the optically active oxazoline compound obtained by the above reaction are shown below.

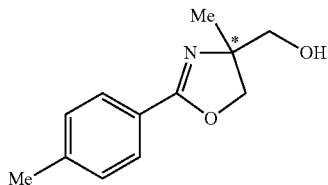 [SMILES: Cc1ccc(C2=NC(C)(CO)CO2)cc1]

white crystal; m.p. 159-162° C.;
$[\alpha]_D^{23}$=+1.7 (c 0.50, $CHCl_3$);
IR (neat): ν=3192 (br), 2963, 2922, 2851, 1645, 1070 $cm^{-1}$;
$^1$H-NMR ($CDCl_3$): δ=1.33 (s, 3H), 2.39 (s, 3H), 3.48 (d, J=11.1 Hz, 1H), 3.76 (d, J=11.4 Hz, 1H), 4.08 (d, J=7.8 Hz, 1H), 4.44 (d, J=8.1 Hz, 1H), 7.19 (d, J=7.8 Hz, 2H), 7.79 (d, J=8.1 Hz, 2H);
$^{13}$C-NMR (400 MHz, $CDCl_3$): δ=164.3, 141.6, 128.8, 128.2, 124.4, 74.5, 71.8, 68.0, 23.7, 21.5;
HPLC: OD-H column (4.6 mmφ, 250 mm), n-Hexane: Isopropanol=100:1, wavelength: 254 nm, flow rate: 1.0 mL/min, retention time: 47.9 min, 62.2 min, 94% ee;
HRMS (M+H, FAB): m/z calcd for $C_{12}H_{16}NO_2$: 206.1181. found: 206.1192.

Example 3

The experiment was conducted in the same manner as in Example 1 except that position 3 of the phenyl group in the starting material was substituted with a methyl group to give (−)-4,5-dihydro-4-hydroxymethyl-4-methyl-2-(3-methylphenyl)oxazole. The yield was 73%. The optical purity was not less than 99% ee ((−)-form).

The structure and the physical property data of the optically active oxazoline compound obtained by the above reaction are shown below.

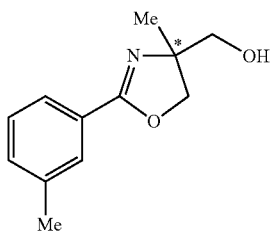 [SMILES: Cc1cccc(C2=NC(C)(CO)CO2)c1]

white crystal; m.p. 63-66° C.;
$[\alpha]_D^{16}$=−5.6 (c 1.00, $CHCl_3$);
IR (neat): ν=3223 (br), 2967, 2924, 2862, 1645, 1072 $cm^{-1}$;
$^1$H-NMR ($CDCl_3$): δ=1.33 (s, 3H), 2.37 (s, 3H), 3.49 (d, J=11.1 Hz, 1H), 3.77 (d, J=11.4 Hz, 1H), 4.09 (d, J=8.1 Hz, 1H), 4.46 (d, J=8.4 Hz, 1H), 7.20-7.34 (m, 2H), 7.66-7.78 (m, 2H);
$^{13}$C-NMR (400 MHz, $CDCl_3$): δ=164.2, 137.6, 131.9, 128.7, 127.9, 126.9, 125.2, 74.4, 71.9, 67.8, 23.7, 21.1;
HPLC: OD-H column (4.6 mmφ, 250 mm), n-Hexane: Isopropanol=20:1, wavelength: 254 nm, flow rate: 0.5 mL/min, retention time: 33.1 min, 73.4 min, >99% ee;
HRMS (M, EI): m/z calcd for $C_{12}H_{15}NO_2$: 205.1098. found: 205.1100.

Example 4

The experiment was conducted in the same manner as in Example 1 except that position 2 of the phenyl group in the starting material was substituted with a methyl group to give (+)-4,5-dihydro-4-hydroxymethyl-4-methyl-2-(2-methylphenyl)oxazole. The yield was 86%. The optical purity was 92% ee ((+)-form).

The structure and the physical property data of the optically active oxazoline compound obtained by the above reaction are shown below.

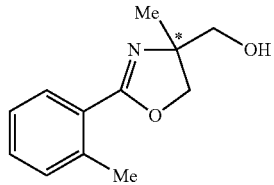 [SMILES: Cc1ccccc1C1=NC(C)(CO)CO1]

white crystal; m.p. 78-80° C.;
$[\alpha]_D^{21}$=+14.2 (c 1.00, $CHCl_3$);
IR (neat): ν=3304 (br), 2967, 2926, 2870, 1639, 1045 $cm^{-1}$;
$^1$H-NMR ($CDCl_3$): δ=1.35 (s, 3H), 1.88 (br, 1H), 2.56 (s, 3H), 3.49 (d, J=10.8 Hz, 1H), 3.75 (d, J=11.1 Hz, 1H), 4.06 (d, J=8.1 Hz, 1H), 4.40 (d, J=8.1 Hz, 1H), 7.18-7.29 (m, 2H), 7.31-7.38 (m, 1H), 7.76 (d, J=7.5 Hz, 1H);
$^{13}$C-NMR (400 MHz, $CDCl_3$): δ=165.1, 138.5, 131.1, 130.6, 129.8, 127.1, 125.5, 74.3, 72.1, 68.1, 23.7, 21.4;
HPLC: OD-H column (4.6 mmφ, 250 mm), n-Hexane: Isopropanol=100:1, wavelength: 254 nm, flow rate: 1.0 mL/min, retention time: 31.8 min, 40.5 min, 92% ee;
HRMS (M+H, EI): m/z calcd for $C_{12}H_{16}NO_2$: 206.1181. found: 206.1171.

Example 5

The experiment was conducted in the same manner as in Example 1 except that position 4 of the phenyl group in the starting material was substituted with a methoxy group to give (−)-4,5-dihydro-4-hydroxymethyl-2-(4-methoxyphenyl)-4-methyloxazole. The yield was 64%. The optical purity was 94% ee ((−)-form).

The structure and the physical property data of the optically active oxazoline compound obtained by the above reaction are shown below.

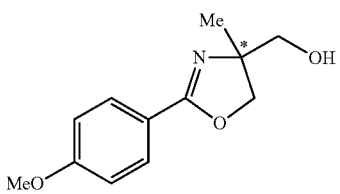 [SMILES: COc1ccc(C2=NC(C)(CO)CO2)cc1]

white crystal; m.p. 111-112° C.;
[α]$_D^{21}$=−20.2 (c 1.00, CHCl$_3$);
IR (neat): ν=3208 (br), 2967, 2941, 2845, 1637, 1252, 1080 cm$^{-1}$;
$^1$H-NMR (CDCl$_3$): δ=1.33 (s, 3H), 3.47 (d, J=11.1 Hz, 1H), 3.75 (d, J=11.4 Hz, 1H), 3.85 (s, 3H), 4.08 (d, J=8.1 Hz, 1H), 4.44 (d, J=8.1 Hz, 1H), 6.86-6.94 (m, 2H), 7.84-7.92 (m, 2H);
$^{13}$C-NMR (400 MHz, CDCl$_3$): δ=164.0, 162.0, 130.0, 119.6, 113.4, 74.5, 71.7, 67.9, 55.3, 23.7;
HPLC: OD-H column (4.6 mmφ, 250 mm), n-Hexane:Isopropanol=20:1, wavelength: 254 nm, flow rate: 1.0 mL/min, retention time: 21.0 min, 37.5 min, 94% ee;
HRMS (M+H, FAB): m/z calcd for C$_{12}$H$_{16}$NO$_3$: 222.1130. found: 222.1130.

Example 6

The experiment was conducted in the same manner as in Example 1 except that position 4 of the phenyl group in the starting material was substituted with a fluorine atom to give (−)-4,5-dihydro-4-hydroxymethyl-2-(4-fluorophenyl)-4-methyloxazole. The yield was 91%. The optical purity was 94% ee ((−)-form).

The structure and the physical property data of the optically active oxazoline compound obtained by the above reaction are shown below.

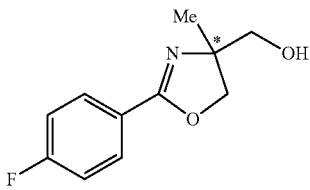

white crystal; m.p. 129-132° C.;
[α]$_D^{19}$=−8.8 (c 1.00, CHCl$_3$);
IR (neat): ν=3184 (br), 2972, 2899, 2855, 1647, 1510, 1070 cm$^{-1}$;
$^1$H-NMR (CDCl$_3$): δ=1.33 (s, 3H), 2.27 (br, 1H), 3.48 (d, J=11.7 Hz, 1H), 3.76 (d, J=11.4 Hz, 1H), 4.08 (d, J=8.1 Hz, 1H), 4.46 (d, J=7.8 Hz, 1H), 7.04-7.12 (m, 2H), 7.88-7.95 (m, 2H);
$^{13}$C-NMR (400 MHz, CDCl$_3$): δ=165.2, 163.2, 163.1, 130.4, 130.3, 123.2, 115.1, 114.9, 74.5, 72.0, 67.5, 23.6;
HPLC: OD-H column (4.6 mmφ, 500 mm), n-Hexane:Isopropanol=100:1, wavelength: 254 nm, flow rate: 1.0 mL/min, retention time: 62.9 min, 71.9 min, 94% ee;
HRMS (M+H, FAB): m/z calcd for C$_{11}$H$_{13}$FNO$_2$: 210.0930. found: 210.0938.

Example 7

The experiment was conducted in the same manner as in Example 1 except that position 4 of the phenyl group in the starting material was substituted with a chlorine atom to give (−)-2-(4-chlorophenyl)-4,5-dihydro-4-hydroxymethyl-4-methyloxazole. The yield was 97%. The optical purity was 96% ee (R enantiomer).

The structure and the physical property data of the optically active oxazoline compound obtained by the above reaction are shown below.

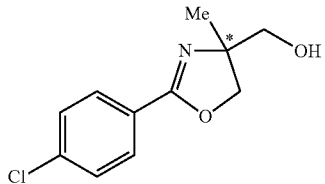 [SMILES: CC1(CO)COC(c2ccc(Cl)cc2)=N1]

white crystal; m.p. 137-139° C.;
[α]$_D^{21}$=−32.2 (c 1.00, CHCl$_3$);
IR (neat): ν=3198 (br), 2967, 2897, 2860, 1651, 1492, 1070 cm$^{-1}$;
$^1$H-NMR (CDCl$_3$): δ=1.33 (s, 3H), 2.27 (br, 1H), 3.49 (t, J=7.8 Hz, 1H), 3.76 (d, J=12.3 Hz, 1H), 4.09 (dd, J=0.9, 8.1 Hz, 1H), 4.47 (d, J=7.8 Hz, 1H), 7.35 (d, J=8.7 Hz, 2H), 7.82 (d, J=8.4 Hz, 2H);
$^{13}$C-NMR (400 MHz, CDCl$_3$): δ=163.2, 137.5, 129.5, 128.3, 125.5, 74.6, 72.1, 67.7, 23.7;
HPLC: AY-H column (4.6 mmφ, 250 mm), n-Hexane:Isopropanol=20:1, wavelength: 254 nm, flow rate: 0.5 mL/min, retention time: 20.8 min, 38.8 min, 96% ee;
HRMS (M+H, FAB): m/z calcd for C$_{11}$H$_{13}$ClNO$_2$: 226.0635. found: 226.0627.

Example 8

The experiment was conducted in the same manner as in Example 1 except that position 4 of the phenyl group in the starting material was substituted with a bromine atom to give (−)-4-(4-bromophenyl)-4,5-dihydro-2-hydroxymethyl-2-methyloxazole. The yield was 98%. The optical purity was 92% ee ((−)-form).

The structure and the physical property data of the optically active oxazoline compound obtained by the above reaction are shown below.

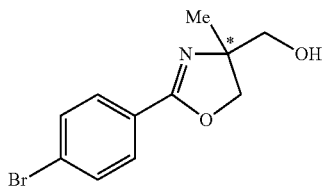

white crystal; m.p. 136-139° C.;
[α]$_D^{19}$=−35.5 (c 1.00, CHCl$_3$);
IR (neat): ν=3219 (br), 2965, 2897, 2862, 1649, 1072 cm$^{-1}$;
$^1$H-NMR (CDCl$_3$): δ=1.33 (s, 3H), 2.16 (br, 1H), 3.44-3.54 (m, 1H), 3.71-3.82 (m, 1H), 4.08 (dd, J=0.6, 8.3 Hz, 1H), 4.54 (d, J=8.1 Hz, 1H), 7.63 (d, J=8.7 Hz, 2H), 7.76 (d, J=8.7 Hz, 2H);
$^{13}$C-NMR (400 MHz, CDCl$_3$): δ=163.3, 131.3, 129.7, 126.0, 125.0, 74.6, 72.1, 67.7, 23.6;
HPLC: OD-H column (4.6 mmφ, 250 mm), n-Hexane:Isopropanol=200:1, wavelength: 254 nm, flow rate: 1.0 mL/min, retention time: 93.4 min, 107.8 min, 92% ee;

HRMS (M+H, FAB): m/z calcd for $C_{11}H_{13}BrNO_2$: 270.0130. found: 270.0153.

Example 9

The experiment was conducted in the same manner as in Example 1 except that position 4 of the phenyl group in the starting material was substituted with an iodine atom to give (−)-4,5-dihydro-4-hydroxymethyl-2-(4-iodophenyl)-4-methyloxazole. The yield was 97%. The optical purity was 87% ee ((−)-form).

The structure and the physical property data of the optically active oxazoline compound obtained by the above reaction are shown below.

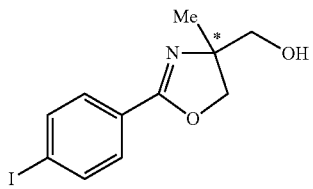 [SMILES: CC1(CO)COC(c2ccc(I)cc2)=N1]

white crystal; m.p. 148-150° C.;
$[\alpha]_D^{18}=-41.4$ (c 1.00, $CHCl_3$);
IR (neat): ν=3221 (br), 2972, 2932, 2854, 1636, 1070 $cm^{-1}$;
$^1$H-NMR ($CDCl_3$): δ=1.32 (s, 3H), 2.17 (br, 1H), 3.42-3.56 (m, 1H), 3.79 (d, J=11.1 Hz, 1H), 4.13 (dd, J=0.6, 8.3 Hz, 1H), 4.49 (d, J=8.1 Hz, 1H), 7.57-7.63 (m, 2H), 7.70-7.76 (m, 2H);
$^{13}$C-NMR (400 MHz, $CDCl_3$): δ=163.5, 137.3, 129.7, 126.5, 98.5, 74.6, 72.1, 67.7, 23.6;
HPLC: OD-H column (4.6 mmφ, 250 mm), n-Hexane:Isopropanol=200:1, wavelength: 254 nm, flow rate: 1.0 mL/min, retention time: 109.0 min, 135.1 min, 87% ee;
HRMS (M+H, EI): m/z calcd for $C_{11}H_{13}INO_2$: 317.9991. found: 317.9986.

Example 10

The experiment was conducted in the same manner as in Example 1 except that position 4 of the phenyl group in the starting material was substituted with a phenyl group to give (−)-4,5-dihydro-4-hydroxymethyl-4-methyl-2-(4-phenylphenyl)oxazole. The yield was 91%. The optical purity was 91% ee ((−)-form).

The structure and the physical property data of the optically active oxazoline compound obtained by the above reaction are shown below.

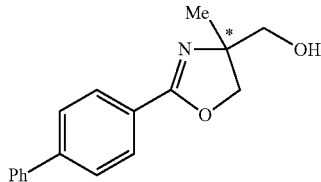

white crystal; m.p. 153-156° C.;
$[\alpha]_D^{20}=-64.6$ (c 1.00, $CHCl_3$);
IR (neat): ν=3221 (br), 2972, 2932, 2907, 1638, 1082 $cm^{-1}$;
$^1$H-NMR ($CDCl_3$): δ=1.31 (s, 3H), 2.32 (br, 1H), 3.48 (d, J=11.4 Hz, 1H), 3.76 (d, J=11.1 Hz, 1H), 4.13 (dd, J=0.6, 8.3 Hz, 1H), 4.46 (d, J=8.1 Hz, 1H), 7.21-7.28 (m, 2H), 7.34-7.50 (m, 2H), 7.62 (d, J=7.8 Hz, 3H), 7.94-8.04 (m, 2H);
$^{13}$C-NMR (400 MHz, $CDCl_3$): δ=164.0, 143.9, 140.2, 128.8, 128.7, 127.9, 127.1, 126.7, 126.0, 74.5, 72.0, 67.9, 23.7;
HPLC: OD-H column (4.6 mmφ, 250 mm), n-Hexane:Isopropanol=100:1, wavelength: 254 nm, flow rate: 1.0 mL/min, retention time: 54.2 min, 72.1 min, 91% ee;
HRMS (M, m/z calcd for $C_{17}H_{17}NO_2$: 267.1259. found: 267.1258.

Example 11

The experiment was conducted in the same manner as in Example 1 except that position 4 of the phenyl group in the starting material was substituted with a nitro group to give (−)-4,5-dihydro-4-hydroxymethyl-4-methyl-2-(4-nitrophenyl)oxazole. The yield was 91%. The optical purity was 93% ee ((−)-form).

The structure and the physical property data of the optically active oxazoline compound obtained by the above reaction are shown below.

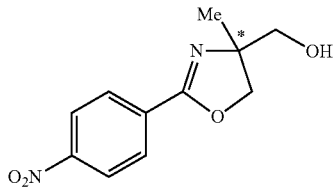 [SMILES: CC1(CO)COC(c2ccc([N+](=O)[O-])cc2)=N1]

white crystal; m.p. 118-120° C.;
$[\alpha]_D^{22}=-9.4$ (c 1.00, $CHCl_3$); IR (neat): ν=3225 (br), 2970, 2933, 2857, 1524, 1078 $cm^{-1}$; $^1$H-NMR ($CDCl_3$): δ=1.36 (s, 3H), 1.60 (br, 1H), 3.48-3.57 (m, 1H), 3.83 (d, J=12.0 Hz, 1H), 4.17 (dd, J=0.9, 8.1 Hz, 1H), 4.48-4.56 (m, 1H), 7.94-8.30 (m, 4H);
$^{13}$C-NMR (400 MHz, $CDCl_3$): δ=162.2, 149.4, 132.9, 129.2, 123.3, 75.1, 72.6, 67.8, 23.6;
HPLC: OD-H column (4.6 mmφ, 250 mm), n-Hexane:Isopropanol=20:1, wavelength: 254 nm, flow rate: 0.5 mL/min, retention time: 52.6 min, 60.5 min, 93% ee;
HRMS (M, EI): m/z calcd for $C_{11}H_{12}N_2O_4$: 236.0797. found: 236.0798.

Example 12

The experiment was conducted in the same manner as in Example 1 except that the methyl group in the starting material was replaced with a hydrogen atom to give (+)-4,5-dihydro-4-hydroxymethyl-2-phenyloxazole. The yield was 32%. The optical purity was 89% ee (R enantiomer).

The structure and the physical property data of the optically active oxazoline compound obtained by the above reaction are shown below.

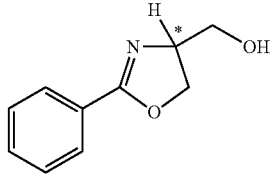

white crystal; m.p. 75-77° C.;

$[\alpha]_D^{22}=+64.2$ (c 0.77, CHCl$_3$); IR (neat): ν=3234 (br), 2910, 2866, 1647, 1062 cm$^{-1}$;

$^1$H-NMR (CDCl$_3$): δ=3.67 (dd, J=2.7 Hz, J=11.7 Hz, 1H), 3.98 (dd, J=3.0 Hz, J=11.7 Hz, 1H), 4.30-4.54 (m, 3H), 7.24-7.52 (m, 3H), 7.85-7.98 (m, 2H);

$^{13}$C-NMR (400 MHz, CDCl$_3$): δ=165.5, 131.4, 128.2, 128.2, 127.1, 69.1, 68.1, 63.7;

HPLC: AY-H column (4.6 mmφ, 250 mm), n-Hexane:Isopropanol=20:1, wavelength: 254 nm, flow rate: 1.0 mL/min, retention time: 18.4 min, 22.9 min, 89% ee;

HMRS (M+H, FAB): m/z calcd for C$_{10}$H$_{12}$NO$_2$: 178.0868. found: 178.0872.

Example 13

The experiment was conducted in the same manner as in Example 1 except that the methyl group in the starting material was replaced with an ethyl group to give (+)-4-ethyl-4,5-dihydro-4-hydroxymethyl-2-phenyloxazole. The yield was 83%. The optical purity was 97% ee ((+)-form).

The structure and the physical property data of the optically active oxazoline compound obtained by the above reaction are shown below.

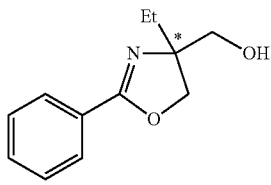 [SMILES: CCC1(CO)COC(c2ccccc2)=N1]

colorless oil;

$[\alpha]_D^{14}=+6.2$ (c 0.945, CHCl$_3$);

IR (neat): ν=3248 (br), 2967, 2928, 2858, 1645, 1067 cm$^{-1}$;

$^1$H-NMR (CDCl$_3$): δ=0.90 (t, J=7.2 Hz, 3H), 1.45-1.80 (m, 2H), 3.50 (d, J=11.7 Hz, 1H), 3.81 (d, J=11.1 Hz, 1H), 4.20 (d, J=8.1 Hz, 1H), 4.39 (d, J=8.4 Hz, 1H), 7.32-7.50 (m, 3H), 7.87 (d, J=8.4 Hz, 1H);

$^{13}$C-NMR (400 MHz, CDCl$_3$): δ=164.1, 131.0, 128.1, 127.9, 126.9, 75.3, 71.8, 66.6, 28.9, 7.4;

HPLC: OD-H column (4.6 mmφ, 250 mm), n-Hexane:Isopropanol=20:1, wavelength: 254 nm, flow rate: 1.0 mL/min, retention time: 16.0 min, 32.8 min, 97% ee;

HMRS (M+H, FAB): m/z calcd for C$_{12}$H$_{16}$NO$_2$: 206.1181. found: 206.1180.

Example 14

The experiment was conducted in the same manner as in Example 1 except that the methyl group in the starting material was replaced with an allyl group to give (+)-4-allyl-4,5-dihydro-4-hydroxymethyl-2-phenyloxazole. The yield was 71%. The optical purity was 92% ee ((+)-form).

The structure and the physical property data of the optically active oxazoline compound obtained by the above reaction are shown below.

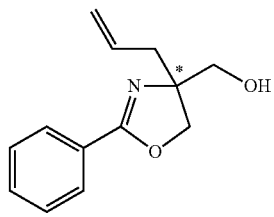 [SMILES: C=CCC1(CO)COC(c2ccccc2)=N1]

colorless oil;

$[\alpha]_D^{17}=+53.8$ (c 0.975, CHCl$_3$);

IR (neat): ν=3238 (br), 3072, 2900, 2860, 1641, 1067 cm$^{-1}$;

$^1$H-NMR (CDCl$_3$): δ=1.23 (br, 1H), 2.20-2.50 (m, 2H), 3.54 (d, J=11.7 Hz, 1H), 3.84 (d, J=11.7 Hz, 1H), 4.24 (d, J=8.7 Hz, 1H), 4.36 (d, J=8.4 Hz, 1H), 5.05-5.20 (m, 2H), 5.60-5.82 (m, 1H), 7.22-7.50 (m, 3H), 7.85 (d, J=7.8 Hz, 2H);

$^{13}$C-NMR (400 MHz, CDCl$_3$): δ=164.6, 132.5, 131.3, 128.2, 128.0, 126.9, 119.0, 74.7, 71.9, 66.8, 40.9;

HPLC: OD-H column (4.6 mmφ, 250 mm), n-Hexane:Isopropanol=20:1, wavelength: 254 nm, flow rate: 0.5 mL/min, retention time: 22.5 min, 62.4 min, 92% ee;

HMRS (M, EI): m/z calcd for C$_{13}$H$_{15}$NO$_2$: 217.1103. found: 217.1103.

Example 15

Production of Optically Active Oxazoline Compound (1)

This experiment was conducted at ordinary temperature and pressure. In 2 mL of tert-butanol, 0.05 mmol of Cu(OTf)$_2$ and 0.05 mmol of (R,R)-Ph-Box were mixed and stirred for 10 minutes. To this, 0.5 mmol of a compound having the structure of the following formula:

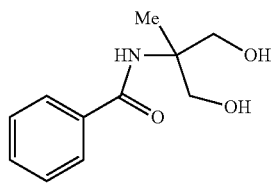 [SMILES: CC(CO)(CO)NC(=O)c1ccccc1]

was added as a starting material.

Then, 1.5 mmol of potassium carbonate was added thereto and finally 1 mmol of p-toluenesulfonyl chloride was added, and the mixture was stirred for 12 hours. After the reaction, water was added and extraction with ethyl acetate was performed 3 times. The organic layer was dried over anhydrous sodium sulfate and filtered, and then the solvent was evaporated off under reduced pressure. The residue was purified by column chromatography (eluent: n-hexane/ethyl acetate=1/1 (v/v)) to give (+)-4,5-dihydro-4-hydroxymethyl-4-methyl-2-phenyloxazole. The yield was 85.0%. The optical purity was 95.4% ee (R enantiomer).

The structure and the physical property data of the optically active oxazoline compound obtained by the above reaction are shown below.

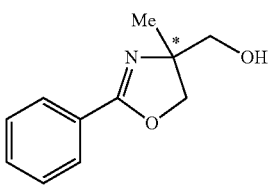 [SMILES: CC1(CO)COC(c2ccccc2)=N1]

white crystal; m.p. 102-104° C.;
[α]$_D^{16}$=+15.2 (c 0.10, CHCl$_3$);
IR (neat): ν=3171 (br), 2972, 2895, 2862, 1641, 1076 cm$^{-1}$;
$^1$H-NMR (CDCl$_3$): δ=1.32 (s, 3H), 3.49 (d, J=11.4 Hz, 1H), 3.78 (d, J=11.1 Hz, 1H), 4.09 (d, J=8.1 Hz, 1H), 4.47 (d, J=8.4 Hz, 1H), 7.33-7.41 (m, 2H), 7.43-7.50 (m, 1H), 7.84-7.91 (m, 2H);
$^{13}$C-NMR (400 MHz, CDCl$_3$): δ=164.1, 131.2, 128.2, 128.0, 127.1, 74.5, 71.9, 67.8, 23.7;
HPLC: OD-H column (4.6 mmφ, 250 mm), n-Hexane:Isopropanol=10:1, wavelength: 254 nm, flow rate: 0.5 mL/min, retention time: 15.3 min, 26.9 min, 95.4% ee;
HRMS (M+H, FAB): m/z calcd for C$_{11}$H$_{14}$NO$_2$: 191.1024. found: 191.1038.

Example 16

The experiment was conducted in the same manner as in Example 15 except that position 4 of the phenyl group in the starting material was substituted with a methyl group to give (+)-4,5-dihydro-4-hydroxymethyl-4-methyl-2-(4-methylphenyl)oxazole. The yield was 89.3%. The optical purity was 94.2% ee ((+)-form).

The structure and the physical property data of the optically active oxazoline compound obtained by the above reaction are shown below.

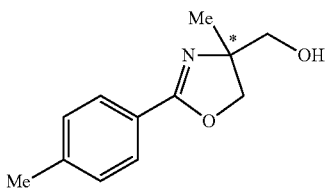

white crystal; m.p. 159-162° C.;
[α]$_D^{23}$=+1.7 (c 0.50, CHCl$_3$);
IR (neat): ν=3192 (br), 2963, 2922, 2851, 1645, 1070 cm$^{-1}$;
$^1$H-NMR (CDCl$_3$): δ=1.33 (s, 3H), 2.39 (s, 3H), 3.48 (d, J=11.1 Hz, 1H), 3.76 (d, J=11.4 Hz, 1H), 4.08 (d, J=7.8 Hz, 1H), 4.44 (d, J=8.1 Hz, 1H), 7.19 (d, J=7.8 Hz, 2H), 7.79 (d, J=8.1 Hz, 2H);
$^{13}$C-NMR (400 MHz, CDCl$_3$): δ=164.3, 141.6, 128.8, 128.2, 124.4, 74.5, 71.8, 68.0, 23.7, 21.5;
HPLC: OD-H column (4.6 mmφ, 250 mm), n-Hexane:Isopropanol=100:1, wavelength: 254 nm, flow rate: 1.0 mL/min, retention time: 47.9 min, 62.2 min, 94.2% ee;
HRMS (M+H, FAB): m/z calcd for C$_{12}$H$_{16}$NO$_2$: 206.1181. found: 206.1192.

Example 17

The experiment was conducted in the same manner as in Example 15 except that position 3 of the phenyl group in the starting material was substituted with a methyl group to give (−)-4,5-dihydro-4-hydroxymethyl-4-methyl-2-(3-methylphenyl)oxazole. The yield was 72.9%. The optical purity was not less than 99% ee ((−)-form).

The structure and the physical property data of the optically active oxazoline compound obtained by the above reaction are shown below.

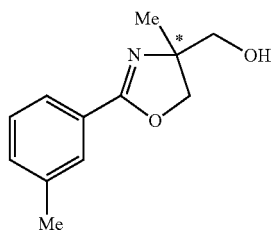 [SMILES: Cc1cccc(C2=NC(C)(CO)CO2)c1]

white crystal; m.p. 63-66° C.;
[α]$_D^{16}$=−5.6 (c 1.00, CHCl$_3$);
IR (neat): ν=3223 (br), 2967, 2924, 2862, 1645, 1072 cm$^{-1}$;
$^1$H-NMR (CDCl$_3$): δ=1.33 (s, 3H), 2.37 (s, 3H), 3.49 (d, J=11.1 Hz, 1H), 3.77 (d, J=11.4 Hz, 1H), 4.09 (d, J=8.1 Hz, 1H), 4.46 (d, J=8.4 Hz, 1H), 7.20-7.34 (m, 2H), 7.66-7.78 (m, 2H);
$^{13}$C-NMR (400 MHz, CDCl$_3$): δ=164.2, 137.6, 131.9, 128.7, 127.9, 126.9, 125.2, 74.4, 71.9, 67.8, 23.7, 21.1;
HPLC: OD-H column (4.6 mmφ, 250 mm), n-Hexane:Isopropanol=20:1, wavelength: 254 nm, flow rate: 0.5 mL/min, retention time: 33.1 min, 73.4 min, >99.9% ee;
HRMS (M, EI): m/z calcd for C$_{12}$H$_{15}$NO$_2$: 205.1098. found: 205.1100.

Example 18

The experiment was conducted in the same manner as in Example 15 except that position 2 of the phenyl group in the starting material was substituted with a methyl group to give (+)-4,5-dihydro-4-hydroxymethyl-4-methyl-2-(2-methylphenyl)oxazole. The yield was 85.8%. The optical purity was 91.9% ee ((+)-form).

The structure and the physical property data of the optically active oxazoline compound obtained by the above reaction are shown below.

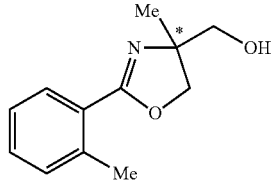 [SMILES: Cc1ccccc1C1=NC(C)(CO)CO1]

white crystal; m.p. 78-80° C.;
[α]$_D^{21}$=+14.2 (c 1.00, CHCl$_3$);
IR (neat): ν=3304 (br), 2967, 2926, 2870, 1639, 1045 cm$^{-1}$;
$^1$H-NMR (CDCl$_3$): δ=1.35 (s, 3H), 1.88 (br, 1H), 2.56 (s, 3H), 3.49 (d, J=10.8 Hz, 1H), 3.75 (d, J=11.1 Hz, 1H), 4.06 (d, J=8.1 Hz, 1H), 4.40 (d, J=8.1 Hz, 1H), 7.18-7.29 (m, 2H), 7.31-7.38 (m, 1H), 7.76 (d, J=7.5 Hz, 1H);
$^{13}$C-NMR (400 MHz, CDCl$_3$): δ=165.1, 138.5, 131.1, 130.6, 129.8, 127.1, 125.5, 74.3, 72.1, 68.1, 23.7, 21.4;

HPLC: OD-H column (4.6 mmφ, 250 mm), n-Hexane:Isopropanol=100:1, wavelength: 254 nm, flow rate: 1.0 mL/min, retention time: 31.8 min, 40.5 min, 91.9% ee;

HRMS (M+H, EI): m/z calcd for $C_{12}H_{16}NO_2$: 206.1181. found: 206.1171.

Example 19

The experiment was conducted in the same manner as in Example 15 except that position 4 of the phenyl group in the starting material was substituted with a methoxy group to give (−)-4,5-dihydro-4-hydroxymethyl-2-(4-methoxyphenyl)-4-methyloxazole. The yield was 63.7%. The optical purity was 93.8% ee ((−)-form).

The structure and the physical property data of the optically active oxazoline compound obtained by the above reaction are shown below.

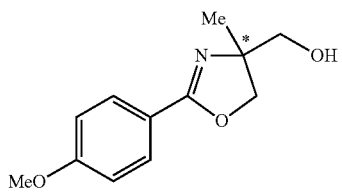 [SMILES: COc1ccc(C2=NC(C)(CO)CO2)cc1]

white crystal; m.p. 111-112° C.;
$[\alpha]_D^{21}=-20.2$ (c 1.00, $CHCl_3$);
IR (neat): ν=3208 (br), 2967, 2941, 2845, 1637, 1252, 1080 $cm^{-1}$;
$^1$H-NMR ($CDCl_3$): δ=1.33 (s, 3H), 3.47 (d, J=11.1 Hz, 1H), 3.75 (d, J=11.4 Hz, 1H), 3.85 (s, 3H), 4.08 (d, J=8.1 Hz, 1H), 4.44 (d, J=8.1 Hz, 1H), 6.86-6.94 (m, 2H), 7.84-7.92 (m, 2H);
$^{13}$C-NMR (400 MHz, $CDCl_3$): δ=164.0, 162.0, 130.0, 119.6, 113.4, 74.5, 71.7, 67.9, 55.3, 23.7;
HPLC: OD-H column (4.6 mmφ, 250 mm), n-Hexane:Isopropanol=20:1, wavelength: 254 nm, flow rate: 1.0 mL/min, retention time: 21.0 min, 37.5 min, 93.8% ee;
HRMS (M+H, FAB): m/z calcd for $C_{12}H_{16}NO_3$: 222.1130. found: 222.1130.

Example 20

The experiment was conducted in the same manner as in Example 15 except that position 4 of the phenyl group in the starting material was substituted with a fluorine atom to give (−)-4,5-dihydro-4-hydroxymethyl-2-(4-fluorophenyl)-4-methyloxazole. The yield was 90.8%. The optical purity was 93.9% ee ((−)-form).

The structure and the physical property data of the optically active oxazoline compound obtained by the above reaction are shown below.

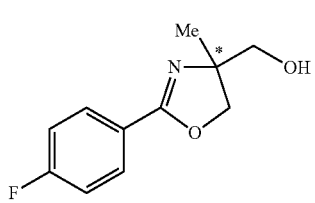

white crystal; m.p. 129-132° C.;
$[\alpha]_D^{19}=-8.8$ (c 1.00, $CHCl_3$);
IR (neat): ν=3184 (br), 2972, 2899, 2855, 1647, 1510, 1070 $cm^{-1}$;
$^1$H-NMR ($CDCl_3$): δ=1.33 (s, 3H), 2.27 (br, 1H), 3.48 (d, J=11.7 Hz, 1H), 3.76 (d, J=11.4 Hz, 1H), 4.08 (d, J=8.1 Hz, 1H), 4.46 (d, J=7.8 Hz, 1H), 7.04-7.12 (m, 2H), 7.88-7.95 (m, 2H);
$^{13}$C-NMR (400 MHz, $CDCl_3$): δ=165.2, 163.2, 163.1, 130.4, 130.3, 123.2, 115.1, 114.9, 74.5, 72.0, 67.5, 23.6;
HPLC: OD-H column (4.6 mmφ, 500 mm), n-Hexane:Isopropanol=100:1, wavelength: 254 nm, flow rate: 1.0 mL/min, retention time: 62.9 min, 71.9 min, 93.9% ee;
HRMS (M+H, FAB): m/z calcd for $C_{11}H_{13}FNO_2$: 210.0930. found: 210.0938.

Example 21

The experiment was conducted in the same manner as in Example 15 except that position 4 of the phenyl group in the starting material was substituted with a chlorine atom to give (−)-2-(4-chlorophenyl)-4,5-dihydro-4-hydroxymethyl-4-methyl oxazole. The yield was 97.3%. The optical purity was 95.6% ee (R enantiomer).

The structure and the physical property data of the optically active oxazoline compound obtained by the above reaction are shown below.

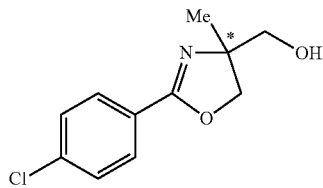 [SMILES: CC1(CO)COC(c2ccc(Cl)cc2)=N1]

white crystal; m.p. 137-139° C.;
$[\alpha]_D^{21}=-32.2$ (c 1.00, $CHCl_3$);
IR (neat): ν=3198 (br), 2967, 2897, 2860, 1651, 1492, 1070 $cm^{-1}$;
$^1$H-NMR ($CDCl_3$): δ=1.33 (s, 3H), 2.27 (br, 1H), 3.49 (t, J=7.8 Hz, 1H), 3.76 (d, J=12.3 Hz, 1H), 4.09 (dd, J=0.9, 8.1 Hz, 1H), 4.47 (d, J=7.8 Hz, 1H), 7.35 (d, J=8.7 Hz, 2H), 7.82 (d, J=8.4 Hz, 2H);
$^{13}$C-NMR (400 MHz, $CDCl_3$): δ=163.2, 137.5, 129.5, 128.3, 125.5, 74.6, 72.1, 67.7, 23.7;
HPLC: AY-H column (4.6 mmφ, 250 mm), n-Hexane:Isopropanol=20:1, wavelength: 254 nm, flow rate: 0.5 mL/min, retention time: 20.8 min, 38.8 min, 95.6% ee;
HRMS (M+H, FAB): m/z calcd for $C_{11}H_{13}ClNO_2$: 226.0635. found: 226.0627.

Example 22

The experiment was conducted in the same manner as in Example 15 except that position 4 of the phenyl group in the starting material was substituted with a bromine atom to give (−)-2-(4-bromophenyl)-4,5-dihydro-4-hydroxymethyl-4-methyloxazole. The yield was 98.1%. The optical purity was 91.6% ee (R enantiomer).

The structure and the physical property data of the optically active oxazoline compound obtained by the above reaction are shown below.

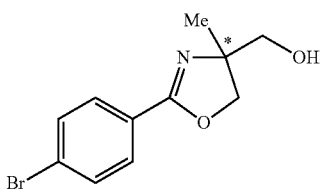

white crystal; m.p. 136-139° C.;
$[\alpha]_D^{19}=-35.5$ (c 1.00, CHCl$_3$);
IR (neat): ν=3219 (br), 2965, 2897, 2862, 1649, 1072 cm$^{-1}$;
$^1$H-NMR (CDCl$_3$): δ=1.33 (s, 3H), 2.16 (br, 1H), 3.44-3.54 (m, 1H), 3.71-3.82 (m, 1H), 4.08 (dd, J=0.6, 8.3 Hz, 1H), 4.54 (d, J=8.1 Hz, 1H), 7.63 (d, J=8.7 Hz, 2H), 7.76 (d, J=8.7 Hz, 2H);
$^{13}$C-NMR (400 MHz, CDCl$_3$): δ=163.3, 131.3, 129.7, 126.0, 125.0, 74.6, 72.1, 67.7, 23.6;
HPLC: OD-H column (4.6 mmφ, 250 mm), n-Hexane:Isopropanol=200:1, wavelength: 254 nm, flow rate: 1.0 mL/min, retention time: 93.4 min, 107.8 min, 91.6% ee;
HRMS (M+H, FAB): m/z calcd for C$_{11}$H$_{13}$BrNO$_2$: 270.0130. found: 270.0153.

Example 23

The experiment was conducted in the same manner as in Example 15 except that position 4 of the phenyl group in the starting material was substituted with an iodine atom to give (−)-4,5-dihydro-4-hydroxymethyl-2-(4-iodophenyl)-4-methyloxazole. The yield was 96.9%. The optical purity was 86.5% ee ((−)-form).

The structure and the physical property data of the optically active oxazoline compound obtained by the above reaction are shown below.

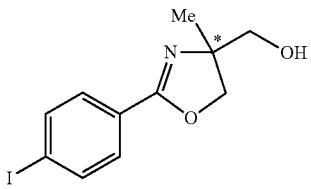 [SMILES: CC1(CO)COC(c2ccc(I)cc2)=N1]

white crystal; m.p. 148-150° C.;
$[\alpha]_D^{18}=-41.4$ (c 1.00, CHCl$_3$);
IR (neat): ν=3221 (br), 2972, 2932, 2854, 1636, 1070 cm$^{-1}$;
$^1$H-NMR (CDCl$_3$): δ=1.32 (s, 3H), 2.17 (br, 1H), 3.42-3.56 (m, 1H), 3.79 (d, J=11.1 Hz, 1H), 4.13 (dd, J=0.6, 8.3 Hz, 1H), 4.49 (d, J=8.1 Hz, 1H), 7.57-7.63 (m, 2H), 7.70-7.76 (m, 2H);
$^{13}$C-NMR (400 MHz, CDCl$_3$): δ=163.5, 137.3, 129.7, 126.5, 98.5, 74.6, 72.1, 67.7, 23.6;
HPLC: OD-H column (4.6 mmφ, 250 mm), n-Hexane:Isopropanol=200:1, wavelength: 254 nm, flow rate: 1.0 mL/min, retention time: 109.0 min, 135.1 min, 86.5% ee;
HRMS (M+H, EI): m/z calcd for C$_{11}$H$_{13}$INO$_2$: 317.9991. found: 317.9986.

Example 24

The experiment was conducted in the same manner as in Example 15 except that position 2 of the phenyl group in the starting material was substituted with an iodine atom to give (+)-4,5-dihydro-4-hydroxymethyl-2-(2-iodophenyl)-4-methyloxazole. The yield was 87.0%. The optical purity was 96.9% ee ((+)-form).

The structure and the physical property data of the optically active oxazoline compound obtained by the above reaction are shown below.

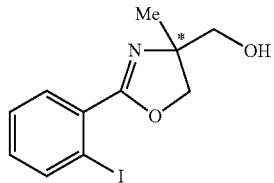 [SMILES: CC1(CO)COC(c2ccccc2I)=N1]

Colorless oil;
$[\alpha]_D^{27}=+25.3$ (c 0.86, CHCl$_3$);
IR (neat): ν=3292 (br), 2967, 2926, 2868, 1654, 1053 cm$^{-1}$;
$^1$H-NMR (CDCl$_3$): δ=1.38 (s, 3H), 3.51 (d, J=11.7 Hz, 1H), 3.80 (d, J=11.1 Hz, 1H), 4.13 (d, J=8.1 Hz, 1H), 4.49 (d, J=8.4 Hz, 1H), 7.13 (dt, J=1.5, 7.5 Hz, 1H), 7.39 (dt, J=1.2, 7.5 Hz, 1H), 7.56 (dd, J=1.9, 7.8 Hz, 1H), 7.93 (dd, J=0.9, 7.8 Hz, 1H);
$^{13}$C-NMR (400 MHz, CDCl$_3$): δ=164.8, 140.1, 133.5, 131.6, 130.3, 127.8, 94.7, 75.1, 72.4, 67.8, 23.3;
HPLC: OD-H column (4.6 mmφ, 250 mm), n-Hexane:Isopropanol=20:1 (+0.1% Et$_2$NH), wavelength: 254 nm, flow rate: 0.5 mL/min, retention time: 23.4 min, 25.3 min, 96.9% ee;
HMRS (M, EI): m/z calcd for C$_{11}$H$_{12}$INO$_2$: 317.9914. found: 317.9904.

Example 25

The experiment was conducted in the same manner as in Example 15 except that position 4 of the phenyl group in the starting material was substituted with a phenyl group to give (−)-4,5-dihydro-4-hydroxymethyl-4-methyl-2-(4-phenylphenyl)oxazole. The yield was 91.1%. The optical purity was 90.6% ee ((−)-form).

The structure and the physical property data of the optically active oxazoline compound obtained by the above reaction are shown below.

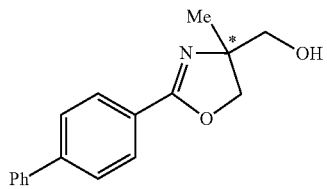

white crystal; m.p. 153-156° C.;
$[\alpha]_D^{20}=-64.6$ (c 1.00, CHCl$_3$);
IR (neat): ν=3221 (br), 2972, 2932, 2907, 1638, 1082 cm$^{-1}$;
$^1$H-NMR (CDCl$_3$): δ=1.31 (s, 3H), 2.32 (br, 1H), 3.48 (d, J=11.4 Hz, 1H), 3.76 (d, J=11.1 Hz, 1H), 4.13 (dd, J=0.6, 8.3 Hz, 1H), 4.46 (d, J=8.1 Hz, 1H), 7.21-7.28 (m, 2H), 7.34-7.50 (m, 2H), 7.62 (d, J=7.8 Hz, 3H), 7.94-8.04 (m, 2H);
$^{13}$C-NMR (400 MHz, CDCl$_3$): δ=164.0, 143.9, 140.2, 128.8, 128.7, 127.9, 127.1, 126.7, 126.0, 74.5, 72.0, 67.9, 23.7;

HPLC: OD-H column (4.6 mmϕ, 250 mm), n-Hexane:Isopropanol=100:1, wavelength: 254 nm, flow rate: 1.0 mL/min, retention time: 54.2 min, 72.1 min, 90.6% ee;

HRMS (M, EI): m/z calcd for $C_{17}H_{17}NO_2$: 267.1259. found: 267.1258.

Example 26

The experiment was conducted in the same manner as in Example 15 except that position 4 of the phenyl group in the starting material was substituted with a nitro group to give (−)-4,5-dihydro-4-hydroxymethyl-4-methyl-2-(4-nitrophenyl)oxazole. The yield was 91.4%. The optical purity was 93.1% ee ((−)-form).

The structure and the physical property data of the optically active oxazoline compound obtained by the above reaction are shown below.

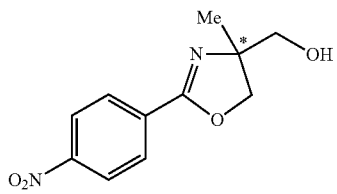

white crystal; m.p. 118-120° C.;

$[\alpha]_D^{22}$=−9.4 (c 1.00, $CHCl_3$);

IR (neat): ν=3225 (br), 2970, 2933, 2857, 1524, 1078 $cm^{-1}$;

$^1$H-NMR ($CDCl_3$): δ=1.36 (s, 3H), 1.60 (br, 1H), 3.48-3.57 (m, 1H), 3.83 (d, J=12.0 Hz, 1H), 4.17 (dd, J=0.9, 8.1 Hz, 1H), 4.48-4.56 (m, 1H), 7.94-8.30 (m, 4H);

$^{13}$C-NMR (400 MHz, $CDCl_3$): δ=162.2, 149.4, 132.9, 129.2, 123.3, 75.1, 72.6, 67.8, 23.6;

HPLC: OD-H column (4.6 mmϕ, 250 mm), n-Hexane:Isopropanol=20:1, wavelength: 254 nm, flow rate: 0.5 mL/min, retention time: 52.6 min, 60.5 min, 93.1% ee;

HRMS (M, EI): m/z calcd for $C_{11}H_{12}N_2O_4$: 236.0797. found: 236.0798.

Example 27

The experiment was conducted in the same manner as in Example 15 except that the phenyl group in the starting material was replaced with a naphthyl group to give (−)-4,5-dihydro-4-hydroxymethyl-4-methyl-2-(2-naphthyl)oxazole. The yield was 90.0%. The optical purity was 99.2% ee ((−)-form).

The structure and the physical property data of the optically active oxazoline compound obtained by the above reaction are shown below.

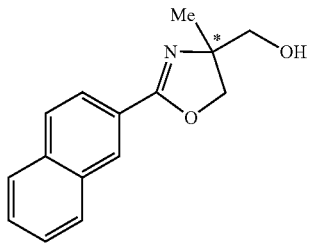 [SMILES: CC1(CO)COC(c2ccc3ccccc3c2)=N1]

white crystal; m.p. 134-136° C.;

$[\alpha]_D^{17}$=−65.5 (c 1.00, $CHCl_3$);

IR (neat): ν=3207 (br), 2967, 2928, 2864, 1645, 1067 $cm^{-1}$;

$^1$H-NMR ($CDCl_3$): δ=1.26 (s, 3H), 1.60 (br, 1H), 3.54 (d, J=11.7 Hz, 1H), 3.83 (d, J=10.8 Hz, 1H), 4.16 (d, J=8.1 Hz, 1H), 4.55 (d, J=7.8 Hz, 1H), 7.43-7.60 (m, 2H), 7.78-7.9 (m, 3H), 7.93-8.02 (m, 1H), 8.31-8.41 (m, 1H);

$^{13}$C-NMR (400 MHz, $CDCl_3$): δ=164.2, 134.5, 132.3, 128.8, 128.8, 127.6, 127.5, 127.4, 126.3, 124.5, 124.2, 74.5, 72.1, 67.9, 23.8;

HPLC: OD-H column (4.6 mmϕ, 250 mm), n-Hexane:Isopropanol=20:1, wavelength: 254 nm, flow rate: 1.0 mL/min, retention time: 23.0 min, 35.4 min, 99.2% ee;

HMRS (M, EI): m/z calcd for $C_{15}H_{15}NO_2$: 241.1103. found: 241.1081.

Example 28

The experiment was conducted in the same manner as in Example 15 except that the phenyl group in the starting material was replaced with a styryl group to give (−)-4,5-dihydro-4-hydroxymethyl-4-methyl-2-styryloxazole. The yield was 20.1%. The optical purity was 94.3% ee ((−)-form).

The structure and the physical property data of the optically active oxazoline compound obtained by the above reaction are shown below.

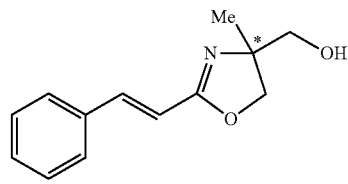 [SMILES: CC1(CO)COC(/C=C/c2ccccc2)=N1]

white crystal; m.p. 89-91° C.;

$[\alpha]_D^{16}$=−43.0 (c 0.935, $CHCl_3$);

IR (neat): ν=3225 (br), 2970, 2933, 2857, 1524, 1078 $cm^{-1}$;

$^1$H-NMR ($CDCl_3$): δ=1.26 (br, 1H), 1.28 (s, 3H), 3.45 (d, J=11.7 Hz, 1H), 3.74 (d, J=11.7 Hz, 1H), 4.02 (d, J=8.1 Hz, 1H), 4.46 (d, J=7.8 Hz, 1H), 6.51 (d, J=16.2 Hz, 1H), 7.19-7.38 (m, 6H);

$^{13}$C-NMR (400 MHz, $CDCl_3$): δ=164.1, 140.5, 134.9, 129.5, 128.7, 127.5, 114.4, 74.5, 71.6, 67.9, 23.5;

HPLC: AY-H column (4.6 mmϕ, 250 mm), n-Hexane:Isopropanol=10:1, wavelength: 254 nm, flow rate: 1.0 mL/min, retention time: 88.4 min, 102.4 min, 94.3% ee;

HMRS (M, m/z calcd for $C_{13}H_{15}NO_2$: 217.1103. found: 217.1083.

Example 29

The experiment was conducted in the same manner as in Example 15 except that the phenyl group in the starting material was replaced with a 2-furyl group to give (+)-4,5-dihydro-2-(2-furyl)-4-hydroxymethyl-4-methyloxazole. The yield was 69.9%. The optical purity was 99.0% ee ((+)-form).

The structure and the physical property data of the optically active oxazoline compound obtained by the above reaction are shown below.

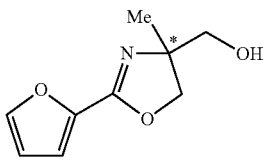 [SMILES: CC1(CO)COC(c2ccco2)=N1]

white crystal; m.p. 85-87° C.;
$[\alpha]_D^{18}$=+6.0 (c 0.5, CHCl$_3$);
IR (neat): ν=3233 (br), 3130, 2968, 2928, 2866, 1670, 1070 cm$^{-1}$;
$^1$H-NMR (CDCl$_3$): δ=1.33 (s, 3H), 2.64 (br, 1H), 3.48 (d, J=11.7 Hz, 1H), 3.78 (d, J=11.7 Hz, 1H), 4.07 (d, J=8.4 Hz, 1H), 4.47 (d, J=8.1 Hz, 1H), 6.42-6.50 (m, 1H), 6.92 (d, J=3.0 Hz, 1H), 7.48-7.54 (m, 2H);
$^{13}$C-NMR (400 MHz, CDCl$_3$): δ=156.3, 145.1, 142.4, 114.6, 111.4, 74.5, 72.1, 67.7, 23.5;
HPLC: AY-H column (4.6 mmφ, 250 mm), n-Hexane:Isopropanol=20:1, wavelength: 254 nm, flow rate: 1.0 mL/min, retention time: 24.7 min, 29.7 min, 99.0% ee;
HMRS (M, EI): m/z calcd for C$_9$H$_{11}$NO$_3$: 181.0739. found: 181.0733.

Example 30

The experiment was conducted in the same manner as in Example 15 except that the phenyl group in the starting material was replaced with a 2-thienyl group to give (+)-4,5-dihydro-4-hydroxymethyl-4-methyl-2-(2-thienyl)oxazole. The yield was 66.8%. The optical purity was 94.0% ee ((+)-form).

The structure and the physical property data of the optically active oxazoline compound obtained by the above reaction are shown below.

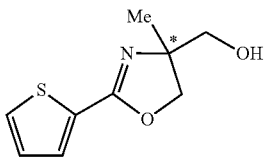 [SMILES: CC1(CO)COC(c2cccs2)=N1]

white crystal; m.p. 132-134° C.;
$[\alpha]_D^{20}$=+3.5 (c 0.5, CHCl$_3$);
IR (neat): ν=3146 (br), 3090, 2976, 2855, 1638, 1078 cm$^{-1}$;
$^1$H-NMR (CDCl$_3$): δ=1.33 (s, 3H), 2.50 (br, 1H), 3.48 (d, J=11.4 Hz, 1H), 3.77 (d, J=11.4 Hz, 1H), 4.09 (d, J=8.4 Hz, 1H), 4.48 (d, J=8.4 Hz, 1H), 7.02-7.08 (m, 1H), 7.44 (dd, J=1.2, 4.8 Hz, 1H), 7.58 (dd, J=0.9, 3.6 Hz, 2H);
$^{13}$C-NMR (400 MHz, CDCl$_3$): δ=159.7, 130.6, 129.9, 129.6, 127.4, 74.9, 72.3, 67.6, 23.6;
HPLC: AY-H column (4.6 mmφ, 250 mm), n-Hexane:Isopropanol=20:1, wavelength: 254 nm, flow rate: 0.5 mL/min, retention time: 29.5 min, 37.4 min, 94.0% ee;
HMRS (M, EI): m/z calcd for C$_9$H$_{11}$NO$_2$S: 197.0510. found: 197.0496.

Example 31

The experiment was conducted in the same manner as in Example 15 except that the phenyl group in the starting material was replaced with a 2-pyrrolyl group to give (−)-4,5-dihydro-4-hydroxymethyl-4-methyl-2-(2-pyrrolyl)oxazole. The yield was 28.1%. The optical purity was 89.2% ee ((−)-form).

The structure and the physical property data of the optically active oxazoline compound obtained by the above reaction are shown below.

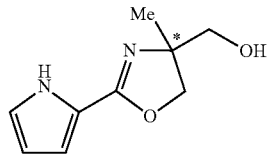 [SMILES: CC1(CO)COC(c2ccc[nH]2)=N1]

colorless oil;
$[\alpha]_D^{24}$=−4.5 (c 1.04 CHCl$_3$);
IR (neat): ν=3217 (br), 3130, 2928, 2872, 1647, 1040 cm$^{-1}$;
$^1$H-NMR (CDCl$_3$): δ=1.38 (s, 3H), 3.54 (d, J=12.3 Hz, 1H), 3.80 (d, J=12.0 Hz, 1H), 4.24 (d, J=8.4 Hz, 1H), 4.61 (d, J=8.4 Hz, 1H), 6.42 (t, J=2.4 Hz, 1H), 6.82 (d, J=3.6 Hz, 1H), 7.05 (s, 1H);
$^{13}$C-NMR (400 MHz, CDCl$_3$): δ=160.9, 126.8, 118.0, 115.9, 111.1, 76.5, 69.1, 66.6, 22.8;
HPLC: AS column (4.6 mmφ, 250 mm), n-Hexane:Ethanol=10:1 (+0.1% Et$_2$NH), wavelength: 254 nm, flow rate: 0.5 mL/min, retention time: 11.7 min, 14.1 min, 89.2% ee;
HMRS (M, EI): m/z calcd for C$_9$H$_{22}$N$_2$O$_2$: 180.0899. found: 180.0895.

Example 32

The experiment was conducted in the same manner as in Example 15 except that the phenyl group in the starting material was replaced with a 3-furyl group to give (+)-4,5-dihydro-2-(3-furyl)-4-hydroxymethyl-4-methyloxazole. The yield was 74.0%. The optical purity was 99.3% ee ((+)-form).

The structure and the physical property data of the optically active oxazoline compound obtained by the above reaction are shown below.

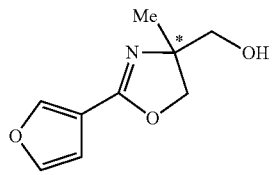 [SMILES: CC1(CO)COC(c2ccoc2)=N1]

white crystal;
m.p. 97-99° C.;
$[\alpha]_D^{24}$=+15.1 (c 0.74, CHCl$_3$); IR (neat): ν=3184 (br), 3113, 2968, 2903, 2859, 1672, 1070 cm$^{-1}$;
$^1$H-NMR (CDCl$_3$): δ=1.26 (s, 3H), 3.44 (d, J=11.7 Hz, 1H), 3.78 (d, J=11.7 Hz, 1H), 4.00 (d, J=8.1 Hz, 1H), 4.45 (d, J=8.1 Hz, 1H), 6.69 (s, 1H), 7.33 (s, 1H), 7.72 (s, 1H);
$^{13}$C-NMR (400 MHz, CDCl$_3$): δ=159.6, 145.1, 143.4, 115.2, 109.3, 74.4, 71.8, 67.8, 23.6;
HPLC: AS column (4.6 mmφ, 250 mm), n-Hexane:Isopropanol=30:1, wavelength: 254 nm, flow rate: 1.0 mL/min, retention time: 13.9 min, 24.2 min, 99.3% ee;
HMRS (M, EI): m/z calcd for C$_9$H$_{11}$NO$_3$: 181.0739. found: 181.0733.

Example 33

The experiment was conducted in the same manner as in Example 15 except that the methyl group in the starting material was replaced with a hydrogen atom to give (+)-4,5-dihydro-4-hydroxymethyl-2-phenyloxazole. The yield was 32.2%. The optical purity was 88.9% ee (R enantiomer).

The structure and the physical property data of the optically active oxazoline compound obtained by the above reaction are shown below.

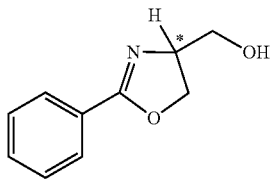 [SMILES: OCC1COC(c2ccccc2)=N1]

white crystal; m.p. 75-77° C.;
$[\alpha]_D^{22}$=+64.2 (c 0.77, CHCl$_3$); IR (neat): ν=3234 (br), 2910, 2866, 1647, 1062 cm$^{-1}$;
$^1$H-NMR (CDCl$_3$): δ=3.67 (dd, J=2.7 Hz, J=11.7 Hz, 1H), 3.98 (dd, J=3.0 Hz, J=11.7 Hz, 1H), 4.30-4.54 (m, 3H), 7.24-7.52 (m, 3H), 7.85-7.98 (m, 2H);
$^{13}$C-NMR (400 MHz, CDCl$_3$): δ=165.5, 131.4, 128.2, 128.2, 127.1, 69.1, 68.1, 63.7;
HPLC: AY-H column (4.6 mmφ, 250 mm), n-Hexane:Isopropanol=20:1, wavelength: 254 nm,
flow rate: 1.0 mL/min, retention time: 18.4 min, 22.9 min, 88.9% ee;
HMRS (M+H, FAB): m/z calcd for C$_{10}$H$_{12}$NO$_2$: 178.0868. found: 178.0872.

Example 34

The experiment was conducted in the same manner as in Example 15 except that the methyl group in the starting material was replaced with an ethyl group to give (+)-4-ethyl-4,5-dihydro-4-hydroxymethyl-2-phenyloxazole. The yield was 82.6%. The optical purity was 97.1% ee ((+)-form).

The structure and the physical property data of the optically active oxazoline compound obtained by the above reaction are shown below.

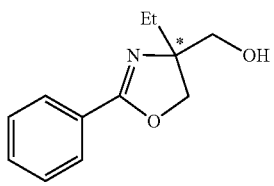 [SMILES: CCC1(CO)COC(c2ccccc2)=N1]

colorless oil;
$[\alpha]_D^{14}$=+6.2 (c 0.945, CHCl$_3$);
IR (neat): ν=3248 (br), 2967, 2928, 2858, 1645, 1067 cm$^{-1}$;
$^1$H-NMR (CDCl$_3$): δ=0.90 (t, J=7.2 Hz, 3H), 1.45-1.80 (m, 2H), 3.50 (d, J=11.7 Hz, 1H), 3.81 (d, J=11.1 Hz, 1H), 4.20 (d, J=8.1 Hz, 1H), 4.39 (d, J=8.4 Hz, 1H), 7.32-7.50 (m, 3H), 7.87 (d, J=8.4 Hz, 1H);
$^{13}$C-NMR (400 MHz, CDCl$_3$): δ=164.1, 131.0, 128.1, 127.9, 126.9, 75.3, 71.8, 66.6, 28.9, 7.4;
HPLC: OD-H column (4.6 mmφ, 250 mm), n-Hexane:Isopropanol=20:1, wavelength: 254 nm, flow rate: 1.0 mL/min, retention time: 16.0 min, 32.8 min, 97.1% ee;
HMRS (M+H, FAB): m/z calcd for C$_{12}$H$_{16}$NO$_2$: 206.1181. found: 206.1180.

Example 35

The experiment was conducted in the same manner as in Example 15 except that the methyl group in the starting material was replaced with an allyl group to give (+)-4-allyl-4,5-dihydro-4-hydroxymethyl-2-phenyloxazole. The yield was 70.8%. The optical purity was 92.3% ee ((+)-form).

The structure and the physical property data of the optically active oxazoline compound obtained by the above reaction are shown below.

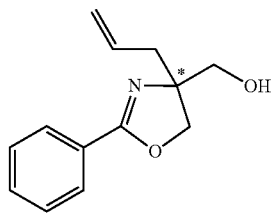 [SMILES: C=CCC1(CO)COC(c2ccccc2)=N1]

colorless oil;
$[\alpha]_D^{17}$=+53.8 (c 0.975, CHCl$_3$);
IR (neat): ν=3238 (br), 3072, 2900, 2860, 1641, 1067 cm$^{-1}$;
$^1$H-NMR (CDCl$_3$): δ=1.23 (br, 1H), 2.20-2.50 (m, 2H), 3.54 (d, J=11.7 Hz, 1H), 3.84 (d, J=11.7 Hz, 1H), 4.24 (d, J=8.7 Hz, 1H), 4.36 (d, J=8.4 Hz, 1H), 5.05-5.20 (m, 2H), 5.60-5.82 (m, 1H), 7.22-7.50 (m, 3H), 7.85 (d, J=7.8 Hz, 2H);
$^{13}$C-NMR (400 MHz, CDCl$_3$): δ=164.6, 132.5, 131.3, 128.2, 128.0, 126.9, 119.0, 74.7, 71.9, 66.8, 40.9;
HPLC: OD-H column (4.6 mmφ, 250 mm), n-Hexane:Isopropanol=20:1, wavelength: 254 nm, flow rate: 0.5 mL/min, retention time: 22.5 min, 62.4 min, 92.3% ee;
HMRS (M, EI): m/z calcd for C13H15NO2: 217.1103. found: 217.1103.

Example 36

The experiment was conducted in the same manner as in Example 15 except that the methyl group in the starting material was replaced with a benzyl group to give (+)-4-benzyl-4,5-dihydro-4-hydroxymethyl-2-phenyloxazole. The yield was 62.3%. The optical purity was 90.6% ee ((+)-form).

The structure and the physical property data of the optically active oxazoline compound obtained by the above reaction are shown below.

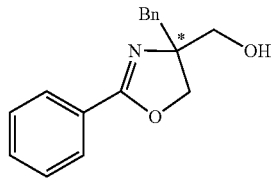

colorless oil;
$[\alpha]_D^{17}$=+101.4 (c 1.24, CHCl$_3$);

IR (neat): ν=3246 (br), 3062, 2920, 2858, 1645, 1066 cm$^{-1}$;

$^1$H-NMR (CDCl$_3$): δ=1.23 (br, 1H), 2.90 (dd, J=33.9, 13.8 Hz, 2H), 3.56 (d, J=11.7 Hz, 1H), 3.90 (d, J=11.7 Hz, 1H), 4.28 (d, J=7.2 Hz, 2H), 7.14-7.32 (m, 7H), 7.35-7.43 (m, 1H), 7.70 (d, J=7.9 Hz, 2H);

$^{13}$C-NMR (400 MHz, CDCl$_3$): δ=164.7, 136.0, 131.2, 130.5, 128.2, 128.1, 128.1, 127.0, 126.6, 75.5, 71.7, 67.1, 42.3;

HPLC: OD-H column (4.6 mmφ, 250 mm), n-Hexane:Isopropanol=20:1, wavelength: 254 nm, flow rate: 1.0 mL/min, retention time: 12.0 min, 27.1 min, 90.6% ee;

HMRS (M, EI): m/z calcd for C$_{17}$H$_{17}$NO$_2$: 267.1260. found: 267.1271.

Example 37

Optical Resolution of Oxazoline

This experiment was conducted at ordinary temperature and pressure. In 2 mL of tert-butanol, 0.03 mmol of Cu(OTf)$_2$ and 0.03 mmol of (R,R)-Ph-Box were mixed and stirred for 10 minutes. To this, 0.3 mmol of a racemic mixture of a compound represented by the following formula:

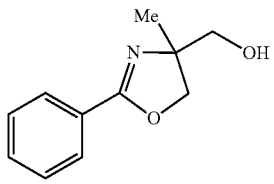 [SMILES: CC1(CO)COC(c2ccccc2)=N1]

was added as a starting material.

Then, 0.45 mmol of potassium carbonate was added thereto and finally 0.36 mmol of p-toluenesulfonyl chloride was added, and the mixture was stirred for 12 hours. After the reaction, water was added and extraction with ethyl acetate was performed 3 times. The organic layer was dried over anhydrous sodium sulfate and filtered, and then the solvent was evaporated off under reduced pressure. The residue was purified by column chromatography (eluent: n-hexane/ethyl acetate=1/1 (v/v)) to give
(+)-4,5-dihydro-4-hydroxymethyl-4-methyl-2-phenyloxazole (yield: 40%, optical purity: 95% ee) and
(−)-4,5-dihydro-4-methyl-2-phenyl-4-tosyloxymethyloxazole (yield: 60%, optical purity: 60% ee).

The structure and the physical property data of the product obtained by the above reaction are shown below.

(+)-4,5-dihydro-4-hydroxymethyl-4-methyl-2-phenyloxazole

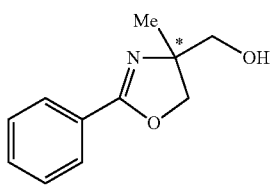 [SMILES: CC1(CO)COC(c2ccccc2)=N1]

white crystal; m.p. 102-104° C.;
[α]$_D^{21}$=+15.2 (c 0.10, CHCl$_3$);

IR (neat): ν=3171 (br), 2972, 2895, 2862, 1641, 1076 cm$^{-1}$;

$^1$H-NMR (CDCl$_3$): δ=1.32 (s, 3H), 3.49 (d, J=11.4 Hz, 1H), 3.78 (d, J=11.1 Hz, 1H), 4.09 (d, J=8.1 Hz, 1H), 4.47 (d, J=8.4 Hz, 1H), 7.33-7.41 (m, 2H), 7.43-7.50 (m, 1H), 7.84-7.91 (m, 2H);

$^{13}$C-NMR (400 MHz, CDCl$_3$): δ=164.1, 131.2, 128.2, 128.0, 127.1, 74.5, 71.9, 67.8, 23.7;

HPLC: OD-H column (4.6 mmφ, 250 mm), n-Hexane:Isopropanol=10:1, wavelength: 254 nm, flow rate: 0.5 mL/min, retention time: 15.3 min, 26.9 min, 95% ee;

HMRS (M+H, FAB): m/z calcd for C$_{11}$H$_{14}$NO$_2$: 191.1024. found: 191.1038.

(−)-4,5-dihydro-4-methyl-2-phenyl-4-tosyloxymethyloxazole

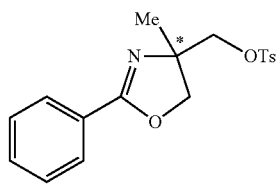 [SMILES: Cc1ccc(S(=O)(=O)OCC2(C)COC(c3ccccc3)=N2)cc1]

white crystal; m.p. 85-87° C.;
[α]$_D^{19}$=−35.4 (c 1.00, CHCl$_3$);

IR (neat): ν=3061, 2974, 2903, 2901, 1645, 1358, 1175 cm$^{-1}$;

$^1$H-NMR (CDCl$_3$): δ=1.36 (s, 3H), 2.42 (s, 1H), 3.94-4.06 (m, 3H), 4.43 (d, J=9.0 Hz, 1H), 4.50 (d, J=8.7 Hz, 1H), 7.20-7.52 (m, 5H), 7.72-7.78 (m, 2H), 7.82-7.88 (m, 2H);

$^{13}$C-NMR (400 MHz, CDCl$_3$): δ=164.5, 144.9, 132.5, 131.6, 129.8, 128.3, 128.2, 127.9, 127.1, 75.0, 74.2, 69.8, 23.6, 21.6;

HPLC: OD-H column (4.6 mmφ, 250 mm), n-Hexane:Isopropanol=10:1, wavelength: 254 nm, flow rate: 0.5 mL/min, retention time: 16.7 min, 25.8 min, 60% ee;

HMRS (M, EI): m/z calcd for C$_{18}$H$_{19}$NO$_4$S: 345.1035. found: 345.1038.

Example 38

Production of Optically Active Oxazoline Compound (2)

This experiment was conducted at room temperature and normal pressure. In 2 mL of acetonitrile, 0.05 mmol of Cu(OTf)$_2$ and 0.05 mmol of (R,R)-Ph-Box were mixed and stirred for 10 minutes. To this, 0.5 mmol of a compound having the structure of the following formula:

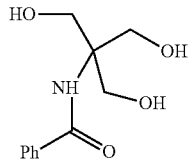

was added as a starting material.

Then, 2.0 mmol of sodium carbonate was added thereto and finally 1.5 mmol of p-toluenesulfonyl chloride was added, and the mixture was stirred at room temperature for 15 hours. After the reaction, water was added and extraction with ethyl acetate was performed 3 times. The organic layer was dried over anhydrous sodium sulfate and filtered, and then the solvent was evaporated off under reduced pressure. The residue was purified by silica gel column chromatography (eluent: n-hexane/ethyl acetate=1/1 (v/v)).

The structure and the physical property data of the product obtained by the above reaction are shown below.

(−)-4,5-dihydro-4-hydroxymethyl-2-phenyl-4-tosyloxymethyloxazole

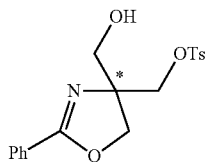 [SMILES: Cc1ccc(S(=O)(=O)OCC2(CO)COC(c3ccccc3)=N2)cc1]

white crystal;
m.p. 75-78° C.;
$[\alpha]_D^{21}$=−36.1 (c 0.50, CHCl$_3$);
IR (neat): ν=3229 (br), 2957, 1626, 1358, 1169 cm$^{-1}$;
$^1$H-NMR (CDCl$_3$): δ=2.57 (s, 3H), 3.62 (d, J=11.7 Hz, 1H), 3.73 (d, J=11.7 Hz, 1H), 4.04 (d, J=9.9 Hz, 1H), 4.17 (d, J=9.9 Hz, 1H), 4.29 (d, J=9.3 Hz, 1H), 4.39 (d, J=9.0 Hz, 1H), 7.27-7.41 (m, 4H), 7.44-7.52 (m, 1H), 7.72-7.85 (m, 4H);
$^{13}$C-NMR (400 MHz, CDCl$_3$): δ=166.4, 145.1, 132.3, 132.0, 129.9, 128.5, 128.3, 128.0, 126.6, 74.4, 71.3, 71.0, 64.7, 21.6;
HPLC: OD-H column (4.6 mmφ, 250 mm), n-Hexane:Ethanol=10:1, wavelength: 254 nm, flow rate: 1.0 mL/min, retention time: 12.4 min, 23.9 min, 96% ee;
HMRS (M+H, FAB): m/z calcd for C$_{18}$H$_{20}$NO$_5$S: 362.1062. found: 362.1062.

4,4-bis(tosyloxymethyl)-4,5-dihydro-2-phenyloxazole

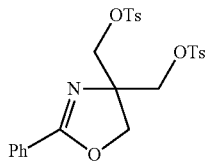 [SMILES: Cc1ccc(S(=O)(=O)OCC2(COS(=O)(=O)c3ccc(C)cc3)COC(c3ccccc3)=N2)cc1]

white crystal;
m.p. 124-126° C.;
IR (neat): ν=2955, 2926, 2857, 2361, 1643, 1362, 1177 cm$^{-1}$;
$^1$H-NMR (CDCl$_3$): δ=2.43 (s, 6H), 4.01 (d, J=10.2 Hz, 2H), 4.12 (d, J=9.9 Hz, 2H), 4.30 (s, 2H), 7.20-7.44 (m, 6H), 7.46-7.54 (m, 1H), 7.68-7.81 (m, 6H);
$^{13}$C-NMR (400 MHz, CDCl$_3$): δ=166.5, 145.2, 132.2, 132.1, 130.0, 128.6, 128.3, 128.0, 126.5, 72.5, 71.2, 71.5, 21.7;
HMRS (M+H, FAB): m/z calcd for C$_{25}$H$_{26}$NO$_7$S$_2$: 516.1151. found: 515.1158.

Example 39

The experiment was conducted in the same manner as in Example 38 except that 1.25 mmol of benzenesulfonyl chloride was used instead of p-toluenesulfonyl chloride.

The structure and the physical property data of the product obtained by the above reaction are shown below.

(−)-4-benzenesulfonyloxymethyl-4,5-dihydro-4-hydroxymethyl-2-phenyloxazole

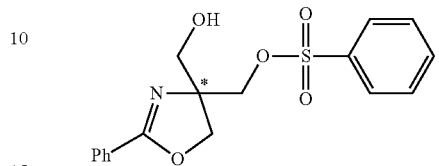

white crystal;
m.p. 118-120° C.;
$[\alpha]_D^{24}$=−31.1 (c 1.22, CHCl$_3$);
IR (neat): ν=3237 (br), 3067, 2905, 2870, 1636, 1360, 1186 cm$^{-1}$;
$^1$H-NMR (CDCl$_3$): δ=3.63 (d, J=10.8 Hz, 1H), 3.74 (d, J=11.4 Hz, 1H), 4.07 (d, J=9.9 Hz, 1H), 4.17 (d, J=9.9 Hz, 1H), 4.29 (d, J=9.3 Hz, 1H), 4.41 (d, J=9.0 Hz, 1H), 7.34-7.43 (m, 2H), 7.45-7.57 (m, 3H), 7.61-7.69 (m, 1H), 7.80-7.93 (m, 4H);
$^{13}$C-NMR (400 MHz, CDCl$_3$): δ=166.5, 135.3, 134.0, 131.9, 129.3, 128.4, 128.2, 127.9, 126.4, 74.3, 71.2, 71.1, 64.5;
HPLC: OD-H column (4.6 mmφ, 250 mm), n-Hexane:Ethanol=10:1, wavelength: 254 nm, flow rate: 1.0 mL/min, retention time: 14.7 min, 29.7 min, 91% ee;
HMRS (M+H, FAB): m/z calcd for C$_{17}$H$_{18}$NO$_5$S: 348.0906. found: 348.0891.

4-bis(benzenesulfonyloxymethyl)-4,5-dihydro-2-phenyloxazole

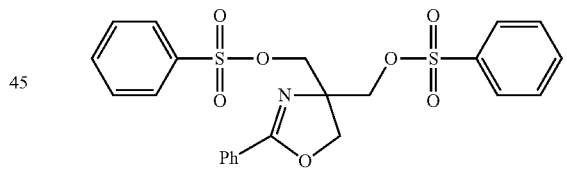

Colorless oil;
IR (neat): ν=3069, 2924, 2855, 1640, 1362, 1188 cm$^{-1}$;
$^1$H-NMR (CDCl$_3$): δ=4.05 (d, J=9.9 Hz, 2H), 4.15 (d, J=9.9 Hz, 2H), 4.30 (s, 2H), 7.20-7.44 (m, 6H), 7.34-7.44 (m, 2H), 7.46-7.57 (m, 4H), 7.61-7.68 (m, 2H), 7.74-7.81 (m, 2H), 7.82-7.90 (m, 3H);
$^{13}$C-NMR (400 MHz, CDCl$_3$): δ=166.6, 135.2, 134.1, 132.2, 129.4, 128.6, 128.3, 128.0, 126.4, 72.5, 71.2, 70.7;
HMRS (M+H, FAB): m/z calcd for C$_{23}$H$_{22}$NO$_7$S$_2$: 488.0838. found: 488.0828.

Example 40

The experiment was conducted in the same manner as in Example 38 except that 1.25 mmol of p-chlorobenzenesulfonyl chloride was used instead of p-toluenesulfonyl chloride.

The structure and the physical property data of the product obtained by the above reaction are shown below.

(−)-4-(4-chlorobenzenesulfonyloxymethyl)-4,5-dihydro-4-hydroxymethyl-2-phenyloxazole

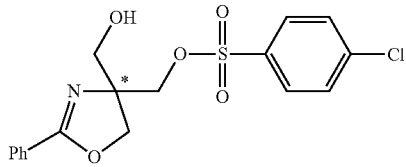 [SMILES: O=S(=O)(OCC1(CO)COC(c2ccccc2)=N1)c1ccc(Cl)cc1]

white crystal;
m.p. 121-122° C.;
$[\alpha]_D^{19}=-38.0$ (c 1.695, $CHCl_3$);
IR (neat): ν=3254 (br), 2959, 1639, 1362, 1186 $cm^{-1}$;
$^1$H-NMR ($CDCl_3$): δ=3.63 (d, J=10.8 Hz, 1H), 3.73 (d, J=11.7 Hz, 1H), 4.12 (d, J=8.1 Hz, 1H), 4.19-4.32 (m, 2H), 4.41 (d, J=8.4 Hz, 1H), 7.35-7.55 (m, 5H), 7.74-7.87 (m, 4H);
$^{13}$C-NMR (400 MHz, $CDCl_3$): δ=166.5, 140.7, 133.9, 132.1, 129.6, 129.3, 128.4, 128.3, 126.4, 74.3, 71.4, 71.1, 64.6;
HPLC: OD-H column (4.6 mmφ, 250 mm), n-Hexane: Ethanol=10:1, wavelength: 254 nm, flow rate: 1.0 mL/min, retention time: 13.1 min, 24.8 min, 75% ee;
HMRS (M+H, FAB): m/z calcd for $C_{17}H_{17}ClNO_5S$: 382.0516. found: 382.0519.

4-bis(4-chlorobenzenesulfonyloxymethyl)-4,5-dihydro-2-phenyloxazole

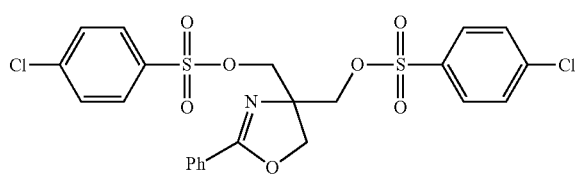 [SMILES: O=S(=O)(OCC1(COS(=O)(=O)c2ccc(Cl)cc2)COC(c2ccccc2)=N1)c1ccc(Cl)cc1]

white crystal;
m.p. 132-134° C.;
IR (neat): ν=3094, 2963, 2909, 2857, 2357, 1643, 1364, 1186 $cm^{-1}$;
$^1$H-NMR ($CDCl_3$): δ=4.08 (d, J=10.2 Hz, 2H), 4.12 (d, J=10.2 Hz, 2H), 4.32 (s, 2H), 7.36-7.56 (m, 6H), 7.70-7.82 (m, 7H);
$^{13}$C-NMR (400 MHz, $CDCl_3$): δ=166.7, 140.9, 133.7, 132.3, 129.7, 129.4, 128.5, 128.4, 126.2, 72.5, 71.2, 70.8;
HMRS (M+H, FAB): m/z calcd for $C_{23}H_{20}Cl_2NO_7S_2$: 556.0059. found: 556.0059.

Example 41

The experiment was conducted in the same manner as in Example 38 except that the phenyl group in the starting material was replaced with a 4-methylphenyl group.

The structure and the physical property data of the product obtained by the above reaction are shown below.

(−)-4,5-dihydro-4-hydroxymethyl-2-(4-methylphenyl)-4-tosyloxymethyloxazole

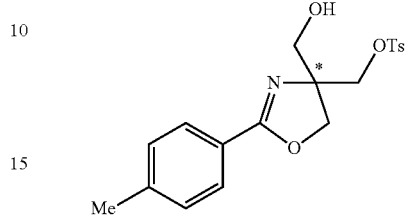

white crystal;
m.p. 121-122° C.;
$[\alpha]_D^{16}=-36.2$ (c 0.50, $CHCl_3$);
IR (neat): ν=3248 (br), 2949, 2924, 1638, 1358, 1173 $cm^{-1}$;
$^1$H-NMR ($CDCl_3$): δ=2.38 (s, 3H), 2.43 (s, 3H), 3.61 (d, J=11.4 Hz, 1H), 3.71 (d, J=11.7 Hz, 1H), 4.02 (d, J=9.9 Hz, 1H), 4.16 (d, J=9.6 Hz, 1H), 4.27 (d, J=9.0 Hz, 1H), 4.37 (d, J=9.0 Hz, 1H), 7.12 (d, J=7.8 Hz, 2H), 7.31 (d, J=8.1 Hz, 2H), 7.70 (d, J=8.1 Hz, 2H), 7.76 (d, J=8.4 Hz, 2H);
$^{13}$C-NMR (400 MHz, $CDCl_3$): δ=166.6, 145.1, 142.5, 132.3, 129.9, 129.0, 128.5, 128.0, 123.8, 74.2, 71.2, 71.0, 65.0, 21.6, 21.6;
HPLC: OD-H column (4.6 mmφ, 250 mm), n-Hexane: Ethanol=10:1, wavelength: 254 nm, flow rate: 1.0 mL/min, retention time: 12.7 min, 15.0 min, 86% ee;
HMRS (M+H, FAB): m/z calcd for $C_{19}H_{22}NO_5S$: 376.1219. found: 376.1209.

4-bis(tosyloxymethyl)-4,5-dihydro-2-(4-methylphenyl)oxazole

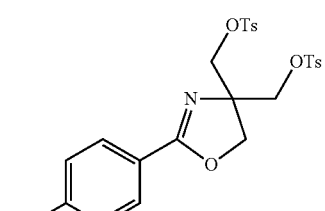

white crystal;
m.p. 110-112° C.;
IR (neat): ν=2955, 2924, 2361, 2342, 1641, 1360, 1175 $cm^{-1}$;
$^1$H-NMR ($CDCl_3$): δ=2.39 (s, 3H), 2.43 (s, 6H), 4.00 (d, J=9.9 Hz, 2H), 4.11 (d, J=9.9 Hz, 2H), 4.28 (s, 2H), 7.18 (d, J=7.8 Hz, 2H), 7.30 (d, J=8.4 Hz, 4H), 7.66 (d, J=8.1 Hz, 2H), 7.72 (d, J=8.4 Hz, 4H);
$^{13}$C-NMR (400 MHz, $CDCl_3$): δ=166.5, 145.2, 142.6, 132.1, 129.9, 129.0, 128.5, 127.9, 123.6, 72.4, 71.1, 70.6, 21.6, 21.6;

HMRS (M+H, FAB): m/z calcd for $C_{26}H_{28}NO_7S_2$: 530.1307. found: 530.1331.

Example 42

The experiment was conducted in the same manner as in Example 38 except that the phenyl group in the starting material was replaced with a 3-methylphenyl group.

The structure and the physical property data of the product obtained by the above reaction are shown below.

(−)-4,5-dihydro-4-hydroxymethyl-2-(3-methylphenyl)-4-tosyloxymethyloxazole

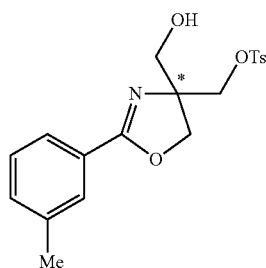 [SMILES: Cc1ccc(S(=O)(=O)OCC2(CO)COC(c3cccc(C)c3)=N2)cc1]

white crystal; m.p. 97-99° C.;
$[\alpha]_D^{19}$=−30.0 (c 0.50, $CHCl_3$);
IR (neat): ν=3244 (br), 2951, 2922, 2359, 2344, 1639, 1358, 1175 $cm^{-1}$;
$^1$H-NMR ($CDCl_3$): δ=2.33 (s, 3H), 2.43 (s, 3H), 3.61 (d, J=11.7 Hz, 1H), 3.72 (d, J=11.4 Hz, 1H), 4.01 (d, J=9.9 Hz, 1H), 4.14 (d, J=9.9 Hz, 1H), 4.29 (d, J=9.0 Hz, 1H), 4.37 (d, J=9.0 Hz, 1H), 7.18-7.34 (m, 4H), 7.53-7.61 (m, 2H), 7.72-7.78 (m, J=8.1 Hz, 2H);
$^{13}$C-NMR (400 MHz, $CDCl_3$): δ=166.6, 145.0, 137.9, 132.6, 132.2, 129.9, 128.9, 128.1, 128.0, 126.3, 125.5, 74.2, 71.1, 71.0, 64.4, 21.6, 21.1;
HPLC: OD-H column (4.6 mmϕ, 250 mm), n-Hexane:Ethanol=10:1, wavelength: 254 nm, flow rate: 1.0 mL/min, retention time: 11.3 min, 29.7 min, 97% ee;
HMRS (M+H, FAB): m/z calcd for $C_{19}H_{22}NO_5S$: 376.1218. found: 376.1210.

4-bis(tosyloxymethyl)-4,5-dihydro-2-(3-methylphenyl)oxazole

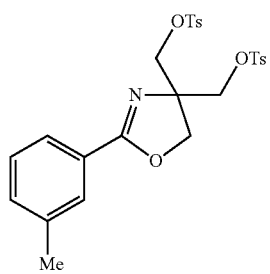 [SMILES: Cc1ccc(S(=O)(=O)OCC2(COS(=O)(=O)c3ccc(C)cc3)COC(c3cccc(C)c3)=N2)cc1]

white crystal;
m.p. 131-133° C.;
IR (neat): ν=2953, 2924, 2853, 2363, 1643, 1360, 1175 $cm^{-1}$;

$^1$H-NMR ($CDCl_3$): δ=2.37 (s, 3H), 2.43 (s, 6H), 4.00 (d, J=10.2 Hz, 2H), 4.11 (d, J=10.2 Hz, 2H), 4.29 (s, 2H), 7.23-7.34 (m, 6H), 7.54-7.64 (m, 2H), 7.70-7.76 (m, 4H);
$^{13}$C-NMR (400 MHz, $CDCl_3$): δ=166.7, 145.2, 138.1, 132.9, 132.1, 129.9, 129.1, 128.2, 128.0, 126.3, 125.7, 72.5, 71.2, 70.6, 21.6, 21.2;
HMRS (M, FAB): m/z calcd for $C_{26}H_{27}NO_7S_2$: 529.1229. found: 529.1221.

Example 43

The experiment was conducted in the same manner as in Example 38 except that the phenyl group in the starting material was replaced with a 2-methylphenyl group.

The structure and the physical property data of the product obtained by the above reaction are shown below.

(−)-4,5-dihydro-4-hydroxymethyl-2-(2-methylphenyl)-4-tosyloxymethyloxazole

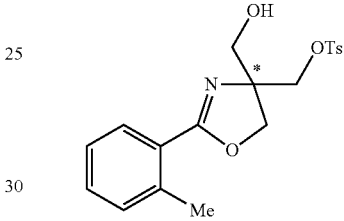

white crystal;
m.p. 103-106° C.;
$[\alpha]_D^{17}$=−31.0 (c 1.275, $CHCl_3$);
IR (neat): ν=3296 (br), 2957, 2926, 2363, 1638, 1358, 1175 $cm^{-1}$;
$^1$H-NMR ($CDCl_3$): δ=2.43 (s, 3H), 2.47 (s, 3H), 3.60 (d, J=11.4 Hz, 1H), 3.71 (d, J=11.1 Hz, 1H), 4.07 (d, J=9.6 Hz, 1H), 4.14-4.25 (m, 2H), 4.34 (d, J=8.7 Hz, 1H), 7.16-7.39 (m, 5H), 7.70 (d, J=7.5 Hz, 1H), 7.77 (m, J=8.4 Hz, 2H);
$^{13}$C-NMR (400 MHz, $CDCl_3$): δ=167.2, 145.1, 138.9, 132.4, 132., 131.1, 129.9, 129.9, 127.9, 126.2, 125.6, 74.6, 71.0, 70.7, 64.8, 21.7, 21.6;
HPLC: OD-H column (4.6 mmϕ, 250 mm), n-Hexane:Ethanol=30:1, wavelength: 254 nm, flow rate: 1.0 mL/min, retention time: 38.5 min, 40.6 min, >99% ee;
HMRS (M+H, FAB): m/z calcd for $C_{19}H_{22}NO_5S$: 376.1218. found: 376.1222.

4-bis(tosyloxymethyl)-4,5-dihydro-2-(2-methylphenyl)oxazole

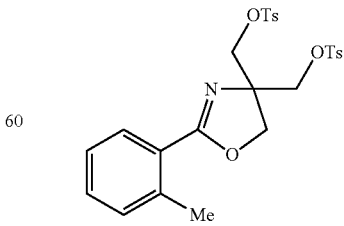

white crystal;
m.p. 64-67° C.;

IR (neat): ν=2956, 2922, 2853, 2361, 1636, 1362, 1177 cm$^{-1}$;

$^1$H-NMR (CDCl$_3$): δ=2.41 (s, 3H), 2.43 (s, 6H), 2.69 (s, 1H), 4.03 (d, J=9.9 Hz, 2H), 4.12 (d, J=9.9 Hz, 2H), 4.26 (s, 2H), 7.15-7.39 (m, 7H), 7.62-7.69 (m, 1H), 7.74 (d, J=8.4 Hz, 4H);

$^{13}$C-NMR (400 MHz, CDCl$_3$): δ=167.2, 145.2, 139.3, 132.2, 131.3, 130.0, 129.6, 128.0, 127.8, 125.9, 125.5, 72.9, 70.6, 70.5, 21.8, 21.7;

HMRS (M+H, FAB): m/z calcd for C$_{25}$H$_{28}$NO$_7$S$_2$: 530.1307. found: 530.1319.

Example 44

The experiment was conducted in the same manner as in Example 38 except that the phenyl group in the starting material was replaced with a 4-chlorophenyl group.

The structure and the physical property data of the product obtained by the above reaction are shown below.

(−)-2-(4-chlorophenyl)-4,5-dihydro-4-hydroxymethyl-4-tosyloxymethyloxazole

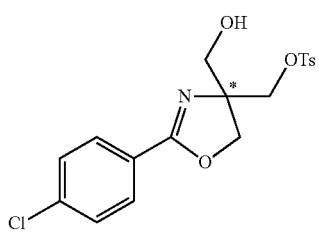 [SMILES: Cc1ccc(S(=O)(=O)OCC2(CO)COC(c3ccc(Cl)cc3)=N2)cc1]

white crystal;

m.p. 128-130° C.;

[α]$_D^{17}$=−25.8 (c 0.50, CHCl$_3$);

IR (neat): ν=3331 (br), 3065, 2926, 2868, 2359, 1651, 1362, 1173 cm$^{-1}$;

$^1$H-NMR (CDCl$_3$): δ=2.09 (br, 1H), 2.44 (s, 3H), 3.60-3.78 (m, 2H), 4.05 (d, J=9.6 Hz, 1H), 4.17 (d, J=9.9 Hz, 1H), 4.29 (d, J=9.0 Hz, 1H), 4.40 (d, J=9.3 Hz, 1H), 7.23-7.40 (m, 4H), 7.73-7.82 (m, 4H);

$^{13}$C-NMR (400 MHz, CDCl$_3$): δ=165.5, 145.2, 138.3, 132.3, 129.9, 129.8, 128.6, 128.0, 125.1, 74.5, 71.5, 70.9, 64.7, 21.7;

HPLC: AY-H column (4.6 mmφ, 250 mm), n-Hexane:Ethanol=10:1, wavelength: 254 nm, flow rate: 1.0 mL/min, retention time: 31.2 min, 41.8 min, 68% ee;

HMRS (M+H, FAB): m/z calcd for C$_{18}$H$_{19}$ClNO$_5$S: 398.0643. found: 398.0660.

4-bis(tosyloxymethyl)-2-(4-chlorophenyl)-4,5-dihydrooxazole

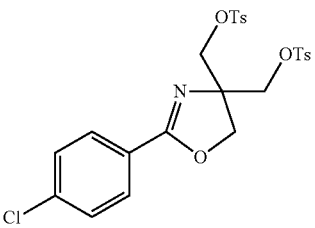 [SMILES: Cc1ccc(S(=O)(=O)OCC2(COS(=O)(=O)c3ccc(C)cc3)COC(c3ccc(Cl)cc3)=N2)cc1]

Colorless oil;

IR (neat): ν=2924, 2857, 2359, 1647, 1364, 1177 cm$^{-1}$;

$^1$H-NMR (CDCl$_3$): δ=2.44 (s, 3H), 4.01 (d, J=9.9 Hz, 2H), 4.11 (d, J=9.9 Hz, 2H), 4.31 (s, 2H), 7.23-7.39 (m, 6H), 7.68-7.75 (m, 6H);

$^{13}$C-NMR (400 MHz, CDCl$_3$): δ=165.6, 145.3, 138.4, 132.2, 130.0, 129.9, 128.6, 128.0, 124.9, 72.7, 71.4, 70.5, 21.7;

HMRS (M+H, FAB): m/z calcd for C$_{25}$H$_{25}$ClNO$_7$S$_2$: 552.0732. found: 552.0740.

Example 45

The experiment was conducted in the same manner as in Example 38 except that the phenyl group in the starting material was replaced with a 2-chlorophenyl group.

The structure and the physical property data of the product obtained by the above reaction are shown below.

(−)-2-(2-chlorophenyl)-4,5-dihydro-4-hydroxymethyl-4-tosyloxymethyloxazole

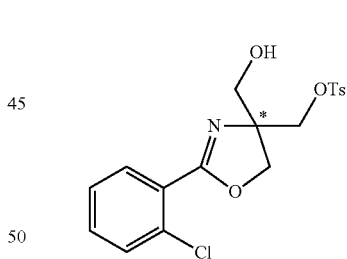

Colorless oil;

[α]$_D^{20}$=−24.0 (c 1.41, CHCl$_3$);

IR (neat): ν=3314 (br), 3067, 2955, 2924, 1647, 1358, 1175 cm$^{-1}$;

$^1$H-NMR (CDCl$_3$): δ=2.43 (s, 3H), 2.57 (br, 1H), 3.61 (d, J=11.4 Hz, 1H), 3.71 (d, J=11.4 Hz, 1H), 4.12 (d, J=9.9 Hz, 1H), 4.18 (d, J=9.9 Hz, 1H), 4.29 (d, J=9.0 Hz, 1H), 4.39 (d, J=9.0 Hz, 1H), 7.24-7.46 (m, 5H), 7.65 (dd, J=1.5, 7.5 Hz, 1H), 7.78 (d, J=8.4 Hz, 2H);

$^{13}$C-NMR (400 MHz, CDCl$_3$): δ=165.1, 145.1, 133.3, 132.3, 132.0, 131.2, 130.6, 129.9, 127.9, 126.6, 126.6, 74.9, 71.3, 70.8, 64.7, 21.6;

HPLC: AY-H column (4.6 mmφ, 250 mm), n-Hexane:Ethanol=4:1, wavelength: 254 nm, flow rate: 1.0 mL/min, retention time: 14.6 min, 27.9 min, 96% ee;

HMRS (M+H, FAB): m/z calcd for $C_{18}H_{19}ClNO_5S$: 398.0643. found: 398.0642.

4-bis(tosyloxymethyl)-2-(2-chlorophenyl)-4,5-dihydrooxazole

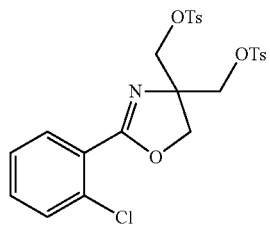 [SMILES: Cc1ccc(S(=O)(=O)OCC2(COS(=O)(=O)c3ccc(C)cc3)COC(c3ccccc3Cl)=N2)cc1]

Colorless oil;
IR (neat): ν=3067, 2957, 2924, 2852, 1645, 1360, 1175 cm$^{-1}$;
$^1$H-NMR (CDCl$_3$): δ=2.44 (s, 3H), 4.06 (d, J=10.2 Hz, 2H), 4.14 (d, J=9.9 Hz, 2H), 4.34 (s, 2H), 7.23-7.45 (m, 7H), 7.79-7.64 (m, 1H), 7.72-7.80 (m, 4H);
$^{13}$C-NMR (400 MHz, CDCl$_3$): δ=165.4, 145.3, 133.5, 132.2, 132.1, 131.5, 130.7, 130.0, 128.0, 126.5, 126.3, 72.9, 71.3, 70.4, 21.7;
HMRS (M+H, FAB): m/z calcd for $C_{25}H_{25}ClNO_7S_2$: 552.0731. found: 552.0718.

Examination on the Type of the Starting Compound in the Production of Optically Active Oxazoline Compound (2)

The structure of the starting compound, and the yield and optical purity of each reaction in Examples 38, and 41 to 44 are shown in Table 1 below. In Table 1, R$^6$ is the substituent bound to position 2 of the oxazoline ring in the starting compound.

TABLE 1

| | R$^6$ | Yield (%) | Optical yield ee (%) | Yield of by-product (%) |
|---|---|---|---|---|
| Example 38 | phenyl | 82 | 96 | 15 |
| Example 41 | 4-methylphenyl | 80 | 86 | 20 |
| Example 42 | 3-methylphenyl | 78 | 97 | 20 |
| Example 43 | 2-methylphenyl | 90 | >99 | 9 |
| Example 44 | 4-chlorolphenyl | 92 | 68 | 4 |
| Example 45 | 2-chlorolphenyl | 79 | 96 | 17 |

Table 1 shows that, regardless of the structure of the triol used as the starting compound, a practical yield and optical purity can be obtained.

Examination on the Type and Amount of the Sulfonyl Halide in the Production of Optically Active Oxazoline Compound (2)

Synthesis of optically active oxazoline compound was performed under the same conditions as in Example 38 except that the type and amount of the sulfonyl halide were varied. The structure and amount of the sulfonyl halide, and the yield and optical purity of each reaction are shown in Table 2 below. In Table 2, the sulfonyl halide is a compound represented by a general formula, R$^7$-Ph-SO$_2$Cl.

The amount of the sulfonyl halide is expressed as molar equivalent relative to 1 mol of the starting compound. The by-product in the table is a compound in which each hydroxyl group bound to a quaternary carbon is protected by the same protecting group.

TABLE 2

| R$^7$ | Amount of sulfonyl halide (eq.) | Yield (%) | Optical yield ee (%) | Yield of by-product (%) |
|---|---|---|---|---|
| 4-Me | 2.2 | 89 | 84 | 4 |
| 4-Me | 2.5 | 85 | 90 | 12 |
| 4-Me (Example 38) | 3.0 | 82 | 96 | 15 |
| 4-Me | 3.5 | 76 | 96 | 21 |
| H | 2.5 | 89 | 91 | 9 |
| H | 3.0 | 78 | 96 | 17 |
| 4-Cl | 2.5 | 64 | 75 | 3 |
| 4-Me* | 3.0 | 88 | 83 | 9 |

*The experiment was conducted under the same conditions as in the others except that the amounts of Cu(OTf)$_2$ and (R, R)—Ph-Box were reduced to half.

Table 2 shows that, regardless of the type and amount of the sulfonyl halide, a practical yield and optical purity can be obtained. It was revealed that, among them, in the case where R$^7$ is 4-Me and the amount of the sulfonyl halide is 2.5 to 3.0 eq., an excellent yield and optical purity can be obtained.

Examination on the Type and Amount of the Base in the Production of Optically Active Oxazoline Compound (2)

Synthesis of optically active oxazoline compounds was performed under the same conditions as in Example 38 except that the amount of the sulfonyl halide is 2.5 mol relative to 1 mol of the starting compound and that the type and amount of the base were varied. The type and amount of the base, and the yield and optical purity of each reaction are shown in Table 3 below.

The amount of the base is expressed as molar equivalent relative to 1 mol of the starting compound. The by-product in the table is a compound in which each hydroxyl group bound to a quaternary carbon is protected by the same protecting group.

TABLE 3

| Base | Amount of base (eq.) | Yield (%) | Optical yield ee (%) | Yield of by-product (%) |
|---|---|---|---|---|
| K$_2$CO$_3$ | 3.5 | 82 | 85 | 5 |
| K$_2$CO$_3$ | 4.0 | 85 | 85 | 5 |
| K$_2$CO$_3$ | 4.5 | 85 | 72 | 5 |
| Na$_2$CO$_3$ | 3.5 | 80 | 89 | 10 |
| Na$_2$CO$_3$ | 4.0 | 85 | 90 | 12 |
| Na$_2$CO$_3$ | 4.5 | 85 | 82 | 10 |

Table 3 shows that, in the cases where K$_2$CO$_3$ or Na$_2$CO$_3$ is used as the base, a practical yield and optical purity can be obtained regardless of the amount of the base.

Examination on the Type and Amount of the Solvent in the Production of Optically Active Oxazoline Compound (2)

Synthesis of optically active oxazoline compounds was performed under the same conditions as in Example 38 except that the amount of the sulfonyl halide is 2.5 mol relative to 1 mol of the starting compound, that potassium carbonate was used instead of sodium carbonate as the base, and that the type of the solvent was varied. The type of the solvent, and the yield and optical purity of each reaction are shown in Table 4 below.

The by-product in the table is a compound in which each hydroxyl group bound to a quaternary carbon is protected by the same protecting group.

TABLE 4

| Solvent | Yield (%) | Optical yield ee (%) | Yield of by-product (%) |
|---|---|---|---|
| MeCN | 85 | 85 | 5 |
| Et$_2$O | 38 | 19 | 4 |
| 1,4-dioxane | 57 | 23 | 4 |
| i-PrOH | 49 | 38 | 9 |
| t-BuOH | 67 | 46 | 2 |
| CH$_2$Cl$_2$ | 62 | 51 | 20 |

Table 4 shows that, in the case where MeCN is used as the solvent, a preferable yield and optical purity can be obtained.

Examination on the Solvent and Base in the Production of Optically Active Oxazoline Compound (2)

Synthesis of optically active oxazoline compounds was performed under the same conditions as in Example 38 except that the amount of the sulfonyl halide is 2.5 mol relative to 1 mol of the starting compound and that types of the solvent and base were varied. The types of the solvent and base, and the yield and optical purity of each reaction are shown in Table 5 below.

The by-product in the table is a compound in which each hydroxyl group bound to a quaternary carbon is protected by the same protecting group.

TABLE 5

| Solvent | Base | Yield (%) | Optical yield ee (%) | Yield of by-product (%) |
|---|---|---|---|---|
| MeCN | K$_2$CO$_3$ | 85 | 85 | 5 |
| 1,4-dioxane | K$_2$CO$_3$ | 57 | 23 | 4 |
| t-BuOH | K$_2$CO$_3$ | 67 | 46 | 2 |
| CH$_2$Cl$_2$ | K$_2$CO$_3$ | 62 | 51 | 20 |
| MeCN | Na$_2$CO$_3$ | 85 | 90 | 12 |
| 1,4-dioxane | Na$_2$CO$_3$ | 47 | 17 | 4 |
| t-BuOH | Na$_2$CO$_3$ | 70 | 45 | 3 |
| CH$_2$Cl$_2$ | Na$_2$CO$_3$ | 68 | 58 | 4 |

Table 5 shows that, in the cases where MeCN (acetonitrile) is used as the solvent, a preferable yield and optical purity can be obtained regardless of the type of base.

INDUSTRIAL APPLICABILITY

According to the present invention, an optically active compound represented by Formula (3) or Formula (4) or a salt thereof, which is an intermediate for the synthesis of various useful compounds, can be produced from an optically inactive compound as a starting compound with fewer production steps. The optically active compound produced according to the present invention is extremely useful as an intermediate for the synthesis of pharmaceuticals, agrochemicals, industrial reagents, etc. In addition, according to the present invention, an optically active compound represented by Formula (8) or a salt thereof can be produced from an optically inactive compound represented by Formula (7) as a starting compound in high yield and high optical purity. In addition, according to the present invention, an optically active compound represented by Formula (8) or a salt thereof can be produced from an optically inactive compound represented by Formula (9) as a starting material in high yield and high optical purity.

Therefore, the present invention is industrially useful.

The invention claimed is:

1. A process for producing an optically active compound represented by Formula (3):

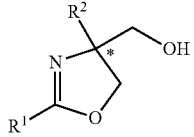

(3)

(wherein R$^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of R$^1$ may be replaced with a substituent; R$^2$ is a hydrogen atom or a group which is not involved in the reaction below; and * represents a chiral center) or a salt thereof by subjecting a compound represented by Formula (1):

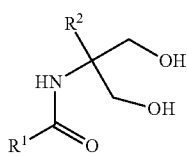

(1)

(wherein R$^1$ and R$^2$ have the same meanings as defined in Formula (3)) to a ring closure reaction in the presence of a chiral ligand having 1 or more coordination sites, a Lewis acid represented by Formula (2):

M$_m$Z$_n$ (2)

(wherein M is a metal ion, Z is a counter anion of M, and m and n are integers of 1 to 4), and a sulfonyl halide having an optionally substituted alkyl or phenyl group.

2. The production process according to claim 1 wherein R$^1$ is an aryl group having 6 to 20 carbon atoms, a 5- to 8-membered monocyclic heteroaryl group or a polycyclic or condensed ring heteroaryl group, each heteroaryl group having 2 to 15 carbon atoms and at least one heteroatom, such as a nitrogen atom, an oxygen atom, and a sulfur atom, or a phenyl group substituted with an alkyl group, an alkenyl group, an alkoxy group, a halogen atom, a nitro group, or an aryl group.

3. The production process according to claim 1 wherein R$^2$ is hydrogen or a hydrocarbon group.

4. The production process according to claim 1 wherein M$_m$Z$_n$ is Cu(OTf)$_2$.

5. The production process according to claim 1 wherein the reaction is performed in the presence of a base.

6. The production process according to claim 1 wherein the reaction is performed in the presence of an organic solvent.

7. An optically active compound represented by Formula (4):

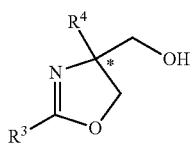

(4)

(wherein R$^3$ is an aryl group having 6 to 20 carbon atoms, a 5- to 8-membered monocyclic heteroaryl group or a polycyclic or condensed ring heteroaryl group, each heteroaryl group having 2 to 15 carbon atoms and at least one heteroatom, such as a nitrogen atom, an oxygen atom, and a sulfur atom, or a phenyl group substituted with an alkyl group, an alkenyl group, an alkoxy group, a halogen atom, a nitro group, or an aryl group and $R^4$ is a hydrogen atom or a group which is not reactive in the reaction, excluding the case where $R^3$ is a phenyl group and $R^4$ is a hydrogen atom or a methyl group; and * represents a chiral center);

or Formula (4)':

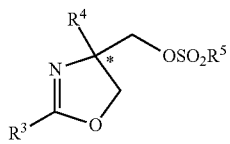

(4')

(wherein $R^3$ and $R^4$ have the same meanings as defined in the above (4); $R^5$ is an optionally substituted alkyl or phenyl group; and * represents a chiral center) or a salt thereof.

8. A process for producing, in an optically selective manner, an (R) or (S) enantiomer of an optically active compound represented by Formula (3):

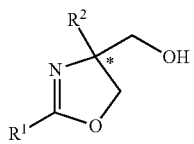

(3)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^2$ is a hydrogen atom or a group which is not reactive in the reaction below; and * represents a chiral center) or a salt thereof and an (R) or (S) enantiomer of an optically active compound represented by Formula (6):

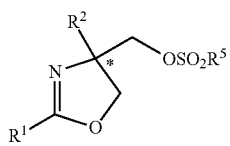

(6)

(wherein $R^1$ and $R^2$ have the same meanings as defined in Formula (3); $R^5$ is an optionally substituted alkyl or phenyl group; and * represents a chiral center) or a salt thereof by subjecting a racemic mixture of a compound represented by Formula (5):

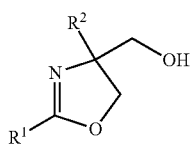

(5)

(wherein $R^1$ and $R^2$ have the same meanings as defined in Formula (3)) to a reaction in the presence of a chiral ligand having 1 or more coordination sites, a Lewis acid represented by Formula (2):

$$M_mZ_n \qquad (2)$$

(wherein M is a metal ion, Z is a counter anion of M, and m and n are integers of 1 to 4), and a sulfonyl halide having an optionally substituted alkyl or phenyl group.

9. A process for producing an optically active compound represented by Formula (8):

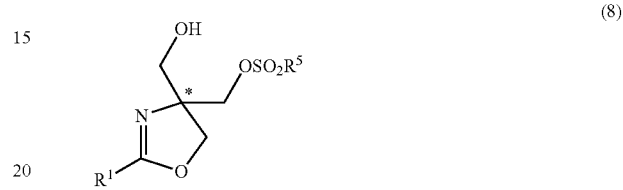

(8)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^5$ is an optionally substituted alkyl or phenyl group; and * represents a chiral center) or a salt thereof by subjecting a compound represented by Formula (7):

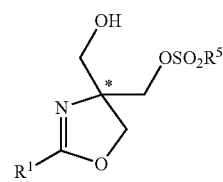

(7)

(wherein $R^1$ has the same meaning as defined in Formula (8)) to a reaction in the presence of a chiral ligand having 1 or more coordination sites, a Lewis acid represented by Formula (2):

$$M_mZ_n \qquad (2)$$

(wherein M is a metal ion, Z is a counter anion of M, and m and n are integers of 1 to 4), and a sulfonyl halide having an optionally substituted alkyl or phenyl group.

10. A process for producing an (R) or (S) enantiomer of an optically active compound represented by Formula (8):

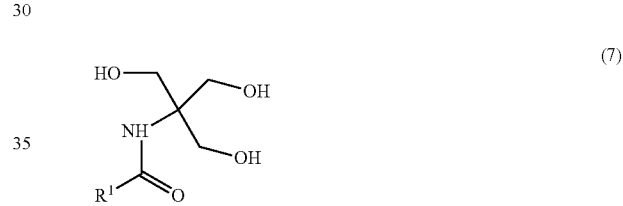

(8)

(wherein $R^1$ is an alkyl group, an alkynyl group, an alkenyl group, an aliphatic heterocyclic group, a cycloalkyl group, an aryl group, an aralkyl group, or an aromatic heterocyclic group, and any hydrogen atom of $R^1$ may be replaced with a substituent; $R^5$ is an optionally substituted alkyl or phenyl group; and * represents a chiral center) or a salt thereof by subjecting a compound represented by Formula (9):

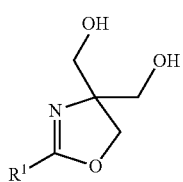
(9)
(wherein $R^1$ has the same meaning as defined in Formula (8)) to a reaction in the presence of a chiral ligand having 1 or more coordination sites, a Lewis acid represented by Formula (2):
$$M_mZ_n \qquad (2)$$
(wherein M is a metal ion, Z is a counter anion of M, and m and n are integers of 1 to 4), and a sulfonyl halide having an optionally substituted alkyl or phenyl group.
* * * * *